US009863042B2

(12) United States Patent
Jones et al.

(10) Patent No.: US 9,863,042 B2
(45) Date of Patent: Jan. 9, 2018

(54) PECVD LUBRICITY VESSEL COATING, COATING PROCESS AND APPARATUS PROVIDING DIFFERENT POWER LEVELS IN TWO PHASES

(71) Applicant: SIO2 MEDICAL PRODUCTS, INC., Auburn, AL (US)

(72) Inventors: Joseph A. Jones, Birmingham, AL (US); John T. Felts, Alameda, CA (US); James Troy Gresham, Opelika, AL (US); Brian Russell Lilly, Auburn, AL (US); Thomas E. Fisk, Green Valley, AZ (US)

(73) Assignee: SiO2 Medical Products, Inc., Auburn, AL (US)

( * ) Notice: Subject to any disclaimer, the term of this patent is extended or adjusted under 35 U.S.C. 154(b) by 423 days.

(21) Appl. No.: 14/214,030

(22) Filed: Mar. 14, 2014

(65) Prior Publication Data

US 2014/0274825 A1    Sep. 18, 2014

Related U.S. Application Data

(60) Provisional application No. 61/792,952, filed on Mar. 15, 2013, provisional application No. 61/800,494, filed on Mar. 15, 2013.

(51) Int. Cl.
*F16C 33/04* (2006.01)
*B05C 11/00* (2006.01)
(Continued)

(52) U.S. Cl.
CPC ...... *C23C 16/45523* (2013.01); *A61L 31/088* (2013.01); *A61L 31/14* (2013.01);
(Continued)

(58) Field of Classification Search
CPC .... F16C 33/201; C23C 16/52; H01J 37/3244; A61B 19/04; H01L 31/202
(Continued)

(56) References Cited

U.S. PATENT DOCUMENTS 3,274,267 A    9/1966 Chow
3,297,465 A    1/1967 Connell
(Continued)

FOREIGN PATENT DOCUMENTS

AU    2002354470 B2    5/2007
CA    2085805           12/1992
(Continued)

OTHER PUBLICATIONS

US 5,645,643, 07/1997, Thomas (withdrawn)
(Continued)

*Primary Examiner* — Vishal Vasisth
(74) *Attorney, Agent, or Firm* — George Wheeler; McAndrews Held & Malloy, Ltd.

(57) ABSTRACT

A method for coating a substrate surface such as a syringe part by PECVD is provided, the method comprising generating a plasma from a gaseous reactant comprising an organosilicon precursor and optionally an oxidizing gas by providing plasma-forming energy adjacent to the substrate, thus forming a coating on the substrate surface by plasma enhanced chemical vapor deposition (PECVD). The plasma-forming energy is applied in a first phase as a first pulse at a first energy level followed by further treatment in a second phase at a second energy level lower than the first energy level. The lubricity, hydrophobicity and/or barrier properties of the coating are set by setting the ratio of the $O_2$ to the organosilicon precursor in the gaseous reactant, and/or by setting the electric power used for generating the plasma.

28 Claims, 6 Drawing Sheets

(51) Int. Cl.
    *C23C 16/50*     (2006.01)
    *A41D 19/00*     (2006.01)
    *C23C 4/04*      (2006.01)
    *B05D 7/24*      (2006.01)
    *H05H 1/24*      (2006.01)
    *C23C 16/455*    (2006.01)
    *A61L 31/08*     (2006.01)
    *C23C 16/32*     (2006.01)
    *A61L 31/14*     (2006.01)
    *A61M 5/31*      (2006.01)
    *A61M 5/28*      (2006.01)
    *C23C 16/40*     (2006.01)
    *C23C 16/515*    (2006.01)
    *C23C 16/505*    (2006.01)
    *C23C 16/511*    (2006.01)
    *A61M 5/32*      (2006.01)

(52) U.S. Cl.
    CPC ............ *A61M 5/28* (2013.01); *A61M 5/3129* (2013.01); *A61M 5/3134* (2013.01); *C23C 16/32* (2013.01); *C23C 16/401* (2013.01); *C23C 16/50* (2013.01); *C23C 16/505* (2013.01); *C23C 16/511* (2013.01); *C23C 16/515* (2013.01); *A61M 5/3202* (2013.01); *A61M 2005/3104* (2013.01); *A61M 2005/3131* (2013.01)

(58) Field of Classification Search
    USPC ........ 508/107; 118/697, 723 R; 427/2.3, 578
    See application file for complete search history.

(56) References Cited

U.S. PATENT DOCUMENTS

| | | |
|---|---|---|
| 3,355,947 A | 12/1967 | Karlby |
| 3,442,686 A | 5/1969 | Jones |
| 3,448,614 A | 6/1969 | Muger |
| 3,590,634 A | 7/1971 | Pasternak |
| 3,838,598 A | 10/1974 | Tompkins |
| 3,957,653 A | 5/1976 | Blecher |
| 4,111,326 A | 9/1978 | Percarpio |
| 4,118,972 A | 10/1978 | Goeppner |
| 4,134,832 A | 1/1979 | Heimreid |
| 4,136,794 A | 1/1979 | Percarpio |
| 4,162,528 A | 7/1979 | Maldonado |
| 4,168,330 A | 9/1979 | Kaganowicz |
| 4,186,840 A | 2/1980 | Percarpio |
| 4,187,952 A | 2/1980 | Percarpio |
| 4,226,333 A | 10/1980 | Percarpio |
| 4,289,726 A | 9/1981 | Potoczky |
| 4,290,534 A | 9/1981 | Percarpio |
| 4,293,078 A | 10/1981 | Percarpio |
| 4,338,764 A | 7/1982 | Percarpio |
| 4,391,128 A | 7/1983 | McWorter |
| 4,392,218 A | 7/1983 | Plunkett, Jr. |
| 4,422,896 A | 12/1983 | Class |
| 4,452,679 A | 6/1984 | Dunn |
| 4,478,873 A | 10/1984 | Masso |
| 4,481,229 A | 11/1984 | Suzuki |
| 4,483,737 A | 11/1984 | Mantei |
| 4,484,479 A | 11/1984 | Eckhardt |
| 4,486,378 A | 12/1984 | Hirata |
| 4,522,510 A | 6/1985 | Rosencwaig |
| 4,524,089 A | 6/1985 | Haque |
| 4,524,616 A | 6/1985 | Drexel |
| 4,552,791 A | 11/1985 | Hahn |
| 4,576,204 A | 3/1986 | Smallborn |
| 4,609,428 A | 9/1986 | Fujimura |
| 4,610,770 A | 9/1986 | Saito |
| 4,648,107 A | 3/1987 | Latter |
| 4,648,281 A | 3/1987 | Morita |
| 4,652,429 A | 3/1987 | Konrad |
| 4,664,279 A | 5/1987 | Obrist |
| 4,667,620 A | 5/1987 | White |
| 4,668,365 A | 5/1987 | Foster |
| 4,683,838 A | 8/1987 | Kimura |
| 4,697,717 A | 10/1987 | Grippi |
| 4,703,187 A | 10/1987 | Hofling |
| 4,716,491 A | 12/1987 | Ohno |
| 4,721,553 A | 1/1988 | Saito |
| 4,725,481 A | 2/1988 | Ostapchenko |
| 4,741,446 A | 5/1988 | Miller |
| 4,756,964 A | 7/1988 | Kincaid |
| 4,767,414 A | 8/1988 | Williams |
| 4,778,721 A | 10/1988 | Sliemers |
| 4,799,246 A | 1/1989 | Fischer |
| 4,808,453 A | 2/1989 | Romberg |
| 4,809,876 A | 3/1989 | Tomaswick |
| 4,810,752 A | 3/1989 | Bayan |
| 4,824,444 A | 4/1989 | Nomura |
| 4,841,776 A | 6/1989 | Kawachi |
| 4,842,704 A | 6/1989 | Collins |
| 4,844,986 A | 7/1989 | Karakelle |
| 4,846,101 A | 7/1989 | Montgomery |
| 4,853,102 A | 8/1989 | Tateishi |
| 4,869,203 A | 9/1989 | Pinkhasov |
| 4,872,758 A | 10/1989 | Miyazaki |
| 4,874,497 A | 10/1989 | Matsuoka |
| 4,880,675 A | 11/1989 | Mehta |
| 4,883,686 A | 11/1989 | Doehler |
| 4,886,086 A | 12/1989 | Etchells |
| 4,894,256 A | 1/1990 | Gartner |
| 4,894,510 A | 1/1990 | Nakanishi |
| 4,897,285 A | 1/1990 | Wilhelm |
| 4,926,791 A | 5/1990 | Hirose |
| 4,948,628 A | 8/1990 | Montgomery |
| 4,973,504 A | 11/1990 | Romberg |
| 4,978,714 A | 12/1990 | Bayan |
| 4,991,104 A | 2/1991 | Miller |
| 4,999,014 A | 3/1991 | Gold |
| 5,000,994 A | 3/1991 | Romberg |
| 5,009,646 A | 4/1991 | Sudo |
| 5,016,564 A | 5/1991 | Nakamura |
| 5,021,114 A | 6/1991 | Saito |
| 5,028,566 A | 7/1991 | Lagendijk |
| 5,030,475 A | 7/1991 | Ackermann |
| 5,032,202 A | 7/1991 | Tsai |
| 5,039,548 A | 8/1991 | Hirose |
| 5,041,303 A | 8/1991 | Wertheimer |
| 5,042,951 A | 8/1991 | Gold |
| 5,044,199 A | 9/1991 | Drexel |
| 5,064,083 A | 11/1991 | Alexander |
| 5,067,491 A | 11/1991 | Taylor |
| 5,079,481 A | 1/1992 | Moslehi |
| 5,082,542 A | 1/1992 | Moslehi |
| 5,084,356 A | 1/1992 | Deak |
| 5,085,904 A | 2/1992 | Deak |
| 5,099,881 A | 3/1992 | Nakajima |
| 5,113,790 A | 5/1992 | Geisler |
| 5,120,966 A | 6/1992 | Kondo |
| 5,131,752 A | 7/1992 | Yu |
| 5,144,196 A | 9/1992 | Gegenwart |
| 5,147,678 A | 9/1992 | Foerch |
| 5,154,943 A | 10/1992 | Etzkorn |
| 5,189,446 A | 2/1993 | Barnes |
| 5,192,849 A | 3/1993 | Moslehi |
| 5,198,725 A | 3/1993 | Chen |
| 5,203,959 A | 4/1993 | Hirose |
| 5,204,141 A | 4/1993 | Roberts |
| 5,209,882 A | 5/1993 | Hattori |
| 5,216,329 A | 6/1993 | Pelleteir |
| 5,224,441 A | 7/1993 | Felts |
| 5,225,024 A | 7/1993 | Hanley |
| 5,232,111 A | 8/1993 | Burns |
| 5,252,178 A | 10/1993 | Moslehi |
| 5,260,095 A | 11/1993 | Affinito |
| 5,266,398 A | 11/1993 | Hioki |
| 5,271,274 A | 12/1993 | Khuri-Yakub |
| 5,272,417 A | 12/1993 | Ohmi |
| 5,272,735 A | 12/1993 | Bryan |
| 5,275,299 A | 1/1994 | Konrad |

(56) References Cited

U.S. PATENT DOCUMENTS

| | | |
|---|---|---|
| 5,286,297 A | 2/1994 | Moslehi |
| 5,288,560 A | 2/1994 | Sudo |
| 5,292,370 A | 3/1994 | Tsai |
| 5,294,011 A | 3/1994 | Konrad |
| 5,294,464 A | 3/1994 | Geisler |
| 5,297,561 A | 3/1994 | Hulon |
| 5,298,587 A | 3/1994 | Hu |
| 5,300,901 A | 4/1994 | Krummel |
| 5,302,266 A | 4/1994 | Grabarz |
| 5,308,649 A | 5/1994 | Babacz |
| 5,314,561 A | 5/1994 | Komiya |
| 5,320,875 A | 6/1994 | Hu |
| 5,321,634 A | 6/1994 | Obata |
| 5,330,578 A | 7/1994 | Sakama |
| 5,333,049 A | 7/1994 | Ledger |
| 5,338,579 A | 8/1994 | Ogawa et al. |
| 5,346,579 A | 9/1994 | Cook |
| 5,354,286 A | 10/1994 | Mesa |
| 5,356,029 A | 10/1994 | Hogan |
| 5,361,921 A | 11/1994 | Burns |
| 5,364,665 A | 11/1994 | Felts |
| 5,364,666 A | 11/1994 | Williams |
| 5,372,851 A | 12/1994 | Ogawa et al. |
| 5,374,314 A | 12/1994 | Babacz |
| 5,378,510 A | 1/1995 | Thomas |
| 5,381,228 A | 1/1995 | Brace |
| 5,395,644 A | 3/1995 | Affinito |
| 5,396,080 A | 3/1995 | Hannotiau |
| 5,397,956 A | 3/1995 | Araki |
| 5,413,813 A | 5/1995 | Cruse |
| 5,423,915 A | 6/1995 | Murata |
| 5,429,070 A | 7/1995 | Campbell |
| 5,433,786 A | 7/1995 | Hu |
| 5,434,008 A | 7/1995 | Felts |
| 5,439,736 A | 8/1995 | Nomura |
| 5,440,446 A | 8/1995 | Shaw |
| 5,443,645 A | 8/1995 | Otoshi |
| 5,444,207 A | 8/1995 | Sekine |
| 5,449,432 A | 9/1995 | Hanawa |
| 5,452,082 A | 9/1995 | Sanger |
| 5,468,520 A | 11/1995 | Williams |
| 5,470,388 A | 11/1995 | Goedicke |
| 5,472,660 A | 12/1995 | Fortin |
| 5,485,091 A | 1/1996 | Verkuil |
| 5,486,701 A | 1/1996 | Norton |
| 5,494,170 A | 2/1996 | Burns |
| 5,494,712 A | 2/1996 | Hu |
| 5,495,958 A | 3/1996 | Konrad |
| 5,508,075 A | 4/1996 | Roulin |
| 5,510,155 A | 4/1996 | Williams |
| 5,513,515 A | 5/1996 | Mayer |
| 5,514,276 A | 5/1996 | Babock |
| 5,521,351 A | 5/1996 | Mahoney |
| 5,522,518 A | 6/1996 | Konrad |
| 5,531,060 A | 7/1996 | Fayet |
| 5,531,683 A | 7/1996 | Kriesel |
| 5,536,253 A | 7/1996 | Haber |
| 5,543,919 A | 8/1996 | Mumola |
| 5,545,375 A | 8/1996 | Tropsha |
| 5,547,508 A | 8/1996 | Affinito |
| 5,547,723 A | 8/1996 | Williams |
| 5,554,223 A | 9/1996 | Imahashi |
| 5,555,471 A | 9/1996 | Xu |
| 5,565,248 A | 10/1996 | Piester |
| 5,569,810 A | 10/1996 | Tsuji |
| 5,571,366 A | 11/1996 | Ishii |
| 5,578,103 A | 11/1996 | Araujo |
| 5,591,898 A | 1/1997 | Mayer |
| 5,593,550 A | 1/1997 | Stewart |
| 5,597,456 A | 1/1997 | Maruyama |
| 5,616,369 A | 4/1997 | Williams |
| 5,620,523 A | 4/1997 | Maeda |
| 5,632,396 A | 5/1997 | Burns |
| 5,633,711 A | 5/1997 | Nelson |
| 5,643,638 A | 7/1997 | Otto |
| 5,652,030 A | 7/1997 | Delperier |
| 5,654,054 A | 8/1997 | Tropsha |
| 5,656,141 A | 8/1997 | Betz |
| 5,658,438 A | 8/1997 | Givens |
| 5,665,280 A | 9/1997 | Tropsha |
| 5,667,840 A | 9/1997 | Tingey |
| 5,674,321 A | 10/1997 | Pu |
| 5,677,010 A | 10/1997 | Esser |
| 5,679,412 A | 10/1997 | Kuehnle |
| 5,679,413 A | 10/1997 | Petrmichl |
| 5,683,771 A | 11/1997 | Tropsha |
| 5,686,157 A | 11/1997 | Harvey |
| 5,690,745 A | 11/1997 | Grunwald |
| 5,691,007 A | 11/1997 | Montgomery |
| 5,693,196 A | 12/1997 | Stewart |
| 5,699,923 A | 12/1997 | Burns |
| 5,702,770 A | 12/1997 | Martin |
| 5,704,983 A | 1/1998 | Thomas et al. |
| 5,716,683 A | 2/1998 | Harvey |
| 5,718,967 A | 2/1998 | Hu |
| 5,725,909 A | 3/1998 | Shaw |
| 5,733,405 A | 3/1998 | Taki |
| 5,736,207 A | 4/1998 | Walther |
| 5,737,179 A | 4/1998 | Shaw |
| 5,738,233 A | 4/1998 | Burns |
| 5,738,920 A | 4/1998 | Knors |
| 5,744,360 A | 4/1998 | Hu |
| 5,750,892 A | 5/1998 | Huang |
| 5,763,033 A | 6/1998 | Tropsha |
| 5,766,362 A | 6/1998 | Montgomery |
| 5,769,273 A | 6/1998 | Sasaki |
| 5,779,074 A | 7/1998 | Burns |
| 5,779,716 A | 7/1998 | Cano |
| 5,779,802 A | 7/1998 | Borghs |
| 5,779,849 A | 7/1998 | Blalock |
| 5,788,670 A | 8/1998 | Reinhard |
| 5,792,550 A | 8/1998 | Phillips |
| 5,792,940 A | 8/1998 | Ghandhi |
| 5,798,027 A | 8/1998 | Lefebvre |
| 5,800,880 A | 9/1998 | Laurent |
| 5,807,343 A | 9/1998 | Tucker |
| 5,807,605 A | 9/1998 | Tingey |
| 5,812,261 A | 9/1998 | Nelson |
| 5,814,257 A | 9/1998 | Kawata |
| 5,814,738 A | 9/1998 | Pinkerton |
| 5,820,603 A | 10/1998 | Tucker |
| 5,823,373 A | 10/1998 | Sudo |
| 5,824,198 A | 10/1998 | Williams |
| 5,824,607 A | 10/1998 | Trow |
| 5,833,752 A | 11/1998 | Martin |
| 5,837,888 A | 11/1998 | Mayer |
| 5,837,903 A | 11/1998 | Weingand |
| 5,840,167 A | 11/1998 | Kim |
| 5,849,368 A | 12/1998 | Hostettler |
| 5,853,833 A | 12/1998 | Sudo |
| 5,855,686 A | 1/1999 | Rust |
| 5,861,546 A | 1/1999 | Sagi |
| 5,871,700 A | 2/1999 | Konrad |
| 5,877,895 A | 3/1999 | Shaw |
| 5,880,034 A | 3/1999 | Keller |
| 5,888,414 A | 3/1999 | Collins |
| 5,888,591 A | 3/1999 | Gleason |
| 5,897,508 A | 4/1999 | Konrad |
| 5,900,284 A | 5/1999 | Hu |
| 5,900,285 A | 5/1999 | Walther |
| 5,902,461 A | 5/1999 | Xu |
| 5,904,952 A | 5/1999 | Lopata |
| 5,913,140 A | 6/1999 | Roche |
| 5,914,189 A | 6/1999 | Hasz |
| 5,919,328 A | 7/1999 | Tropsha |
| 5,919,420 A | 7/1999 | Niermann |
| 5,935,391 A | 8/1999 | Nakahigashi |
| 5,945,187 A | 8/1999 | Buch-Rasmussen |
| 5,951,527 A | 9/1999 | Sudo |
| 5,952,069 A | 9/1999 | Tropsha |
| 5,955,161 A | 9/1999 | Tropsha |
| 5,961,911 A | 10/1999 | Hwang |
| 5,968,620 A | 10/1999 | Harvey |
| 5,972,297 A | 10/1999 | Niermann |

(56) References Cited

U.S. PATENT DOCUMENTS

| | | |
|---|---|---|
| 5,972,436 A | 10/1999 | Walther |
| 5,985,103 A | 11/1999 | Givens |
| 6,001,429 A | 12/1999 | Martin |
| 6,009,743 A | 1/2000 | Mayer |
| 6,013,337 A | 1/2000 | Knors |
| 6,017,317 A | 1/2000 | Newby |
| 6,018,987 A | 2/2000 | Mayer |
| 6,020,196 A | 2/2000 | Hu |
| 6,027,619 A | 2/2000 | Cathey |
| 6,032,813 A | 3/2000 | Niermann |
| 6,035,717 A | 3/2000 | Carodiskey |
| 6,050,400 A | 4/2000 | Taskis |
| 6,051,151 A | 4/2000 | Keller |
| 6,054,016 A | 4/2000 | Tuda |
| 6,054,188 A | 4/2000 | Tropsha |
| 6,068,884 A | 5/2000 | Rose |
| 6,077,403 A | 6/2000 | Kobayashi |
| 6,081,330 A | 6/2000 | Nelson |
| 6,082,295 A | 7/2000 | Lee |
| 6,083,313 A | 7/2000 | Venkatraman et al. |
| 6,085,927 A | 7/2000 | Kusz |
| 6,090,081 A | 7/2000 | Sudo |
| 6,093,175 A | 7/2000 | Gyure |
| 6,106,678 A | 8/2000 | Shufflebotham |
| 6,110,395 A | 8/2000 | Gibson, Jr. |
| 6,110,544 A | 8/2000 | Yang |
| 6,112,695 A | 9/2000 | Felts |
| 6,116,081 A | 9/2000 | Ghandhi |
| 6,117,243 A | 9/2000 | Walther |
| 6,118,844 A | 9/2000 | Fischer |
| 6,124,212 A | 9/2000 | Fan |
| 6,125,687 A | 10/2000 | McClelland |
| 6,126,640 A | 10/2000 | Tucker |
| 6,129,712 A | 10/2000 | Sudo |
| 6,129,956 A | 10/2000 | Morra |
| 6,136,275 A | 10/2000 | Niermann |
| 6,139,802 A | 10/2000 | Niermann |
| 6,143,140 A | 11/2000 | Wang |
| 6,149,982 A | 11/2000 | Plester |
| 6,153,269 A | 11/2000 | Gleason |
| 6,156,152 A | 12/2000 | Ogino |
| 6,156,399 A | 12/2000 | Spallek |
| 6,156,435 A | 12/2000 | Gleason |
| 6,160,350 A | 12/2000 | Sakemi |
| 6,161,712 A | 12/2000 | Savitz |
| 6,163,006 A | 12/2000 | Doughty |
| 6,165,138 A | 12/2000 | Miller |
| 6,165,542 A | 12/2000 | Jaworowski |
| 6,165,566 A | 12/2000 | Tropsha |
| 6,171,670 B1 | 1/2001 | Sudo |
| 6,175,612 B1 | 1/2001 | Sato |
| 6,177,142 B1 | 1/2001 | Felts |
| 6,180,185 B1 | 1/2001 | Felts |
| 6,180,191 B1 | 1/2001 | Felts |
| 6,188,079 B1 | 2/2001 | Juvinall |
| 6,189,484 B1 | 2/2001 | Yin |
| 6,190,992 B1 | 2/2001 | Sandhu |
| 6,193,853 B1 | 2/2001 | Yumshtyk |
| 6,196,155 B1 | 3/2001 | Setoyama |
| 6,197,166 B1 | 3/2001 | Moslehi |
| 6,200,658 B1 | 3/2001 | Walther |
| 6,200,675 B1 | 3/2001 | Neerinck |
| 6,204,922 B1 | 3/2001 | Chalmers |
| 6,210,791 B1 | 4/2001 | Skoog |
| 6,214,422 B1 | 4/2001 | Yializis |
| 6,217,716 B1 | 4/2001 | Fai Lai |
| 6,223,683 B1 | 5/2001 | Plester |
| 6,236,459 B1 | 5/2001 | Negahdaripour |
| 6,245,190 B1 | 6/2001 | Masuda |
| 6,248,219 B1 | 6/2001 | Wellerdieck |
| 6,248,397 B1 | 6/2001 | Ye |
| 6,251,792 B1 | 6/2001 | Collins |
| 6,254,983 B1 | 7/2001 | Namiki |
| 6,261,643 B1 | 7/2001 | Hasz |
| 6,263,249 B1 | 7/2001 | Stewart |
| 6,271,047 B1 | 8/2001 | Ushio |
| 6,276,296 B1 | 8/2001 | Plester |
| 6,277,331 B1 | 8/2001 | Konrad |
| 6,279,505 B1 | 8/2001 | Plester |
| 6,284,986 B1 | 9/2001 | Dietze |
| 6,306,132 B1 | 10/2001 | Moorman |
| 6,308,556 B1 | 10/2001 | Sagi |
| 6,322,661 B1 | 11/2001 | Bailey, III |
| 6,331,174 B1 | 12/2001 | Reinhard et al. |
| 6,344,034 B1 | 2/2002 | Sudo |
| 6,346,596 B1 | 2/2002 | Mallen |
| 6,348,967 B1 | 2/2002 | Nelson |
| 6,350,415 B1 | 2/2002 | Niermann |
| 6,351,075 B1 | 2/2002 | Barankova |
| 6,352,629 B1 | 3/2002 | Wang |
| 6,354,452 B1 | 3/2002 | DeSalvo |
| 6,355,033 B1 | 3/2002 | Moorman |
| 6,365,013 B1 | 4/2002 | Beele |
| 6,375,022 B1 | 4/2002 | Zurcher |
| 6,376,028 B1 | 4/2002 | Laurent |
| 6,379,757 B1 | 4/2002 | Iacovangelo |
| 6,382,441 B1 | 5/2002 | Carano |
| 6,394,979 B1 | 5/2002 | Sharp |
| 6,396,024 B1 | 5/2002 | Doughty |
| 6,399,944 B1 | 6/2002 | Vasilyev |
| 6,402,885 B2 | 6/2002 | Loewenhardt |
| 6,410,926 B1 | 6/2002 | Munro |
| 6,413,645 B1 | 7/2002 | Graff |
| 6,432,494 B1 | 8/2002 | Yang |
| 6,432,510 B1 | 8/2002 | Kim |
| 6,470,650 B1 | 10/2002 | Lohwasser |
| 6,471,822 B1 | 10/2002 | Yin |
| 6,475,622 B2 | 11/2002 | Namiki |
| 6,482,509 B2 | 11/2002 | Buch-Rasmussen et al. |
| 6,486,081 B1 | 11/2002 | Ishikawa |
| 6,500,500 B1 | 12/2002 | Okamura |
| 6,503,579 B1 | 1/2003 | Murakami |
| 6,518,195 B1 | 2/2003 | Collins |
| 6,524,282 B1 | 2/2003 | Sudo |
| 6,524,448 B2 | 2/2003 | Brinkmann |
| 6,539,890 B1 | 4/2003 | Felts |
| 6,544,610 B1 | 4/2003 | Minami |
| 6,551,267 B1 | 4/2003 | Cohen |
| 6,558,679 B2 | 5/2003 | Flament-Garcia et al. |
| 6,562,010 B1 | 5/2003 | Gyure |
| 6,562,189 B1 | 5/2003 | Quiles |
| 6,565,791 B1 | 5/2003 | Laurent |
| 6,582,426 B2 | 6/2003 | Moorman |
| 6,582,823 B1 | 6/2003 | Sakhrani et al. |
| 6,584,828 B2 | 7/2003 | Sagi |
| 6,595,961 B2 | 7/2003 | Hetzler |
| 6,597,193 B2 | 7/2003 | Lagowski |
| 6,599,569 B1 | 7/2003 | Humele |
| 6,599,594 B1 | 7/2003 | Walther |
| 6,602,206 B1 | 8/2003 | Niermann |
| 6,616,632 B2 | 9/2003 | Sharp |
| 6,620,139 B1 | 9/2003 | Plicchi |
| 6,620,334 B2 | 9/2003 | Kanno |
| 6,623,861 B2 | 9/2003 | Martin |
| 6,638,403 B1 | 10/2003 | Inaba |
| 6,638,876 B2 | 10/2003 | Levy |
| 6,645,354 B1 | 11/2003 | Gorokhovsky |
| 6,645,635 B2 | 11/2003 | Muraki |
| 6,651,835 B2 | 11/2003 | Iskra |
| 6,652,520 B2 | 11/2003 | Moorman |
| 6,656,540 B2 | 12/2003 | Sakamoto |
| 6,658,919 B2 | 12/2003 | Chatard |
| 6,662,957 B2 | 12/2003 | Zurcher |
| 6,663,601 B2 | 12/2003 | Hetzler |
| 6,663,603 B1 | 12/2003 | Gyure |
| 6,670,200 B2 | 12/2003 | Ushio |
| 6,673,199 B1 | 1/2004 | Yamartino |
| 6,680,091 B2 | 1/2004 | Buch-Rasmussen et al. |
| 6,680,621 B2 | 1/2004 | Savtchouk |
| 6,683,308 B2 | 1/2004 | Itagaki |
| 6,684,683 B2 | 2/2004 | Potyrailo |
| 6,702,898 B2 | 3/2004 | Hosoi |
| 6,706,412 B2 | 3/2004 | Yializis |
| 6,746,430 B2 | 6/2004 | Lubrecht |

(56) References Cited

U.S. PATENT DOCUMENTS

| | | |
|---|---|---|
| 6,749,078 B2 | 6/2004 | Iskra |
| 6,752,899 B1 | 6/2004 | Singh |
| 6,753,972 B1 | 6/2004 | Hirose |
| 6,757,056 B1 | 6/2004 | Meeks |
| 6,764,714 B2 | 7/2004 | Wei |
| 6,765,466 B2 | 7/2004 | Miyata |
| 6,766,682 B2 | 7/2004 | Engle |
| 6,774,018 B2 | 8/2004 | Mikhael |
| 6,796,780 B1 | 9/2004 | Chatard |
| 6,800,852 B2 | 10/2004 | Larson |
| 6,808,753 B2 | 10/2004 | Rule |
| 6,810,106 B2 | 10/2004 | Sato |
| 6,815,014 B2 | 11/2004 | Gabelnick |
| 6,818,310 B2 | 11/2004 | Namiki |
| 6,822,015 B2 | 11/2004 | Muraki |
| 6,837,954 B2 | 1/2005 | Carano |
| 6,844,075 B1 | 1/2005 | Saak |
| 6,853,141 B2 | 2/2005 | Hoffman |
| 6,858,259 B2 | 2/2005 | Affinito |
| 6,863,731 B2 | 3/2005 | Elsayed-Ali |
| 6,864,773 B2 | 3/2005 | Perrin |
| 6,866,656 B2 | 3/2005 | Tingey |
| 6,872,428 B2 | 3/2005 | Yang |
| 6,876,154 B2 | 4/2005 | Appleyard |
| 6,885,727 B2 | 4/2005 | Tamura |
| 6,887,578 B2 | 5/2005 | Gleason |
| 6,891,158 B2 | 5/2005 | Larson |
| 6,892,567 B1 | 5/2005 | Morrow |
| 6,899,054 B1 | 5/2005 | Bardos |
| 6,905,769 B2 | 6/2005 | Komada |
| 6,910,597 B2 | 6/2005 | Iskra |
| 6,911,779 B2 | 6/2005 | Madocks |
| 6,919,107 B2 | 7/2005 | Schwarzenbach |
| 6,919,114 B1 | 7/2005 | Darras |
| 6,933,460 B2 | 8/2005 | Vanden Brande |
| 6,946,164 B2 | 9/2005 | Huang |
| 6,952,949 B2 | 10/2005 | Moore |
| 6,960,393 B2 | 11/2005 | Yializis |
| 6,962,671 B2 | 11/2005 | Martin |
| 6,965,221 B2 | 11/2005 | Lipcsei |
| 6,981,403 B2 | 1/2006 | Ascheman |
| 6,989,675 B2 | 1/2006 | Kesil |
| 6,995,377 B2 | 2/2006 | Darr |
| 7,029,755 B2 | 4/2006 | Terry |
| 7,029,803 B2 | 4/2006 | Becker |
| 7,039,158 B1 | 5/2006 | Janik |
| 7,052,736 B2 | 5/2006 | Wei |
| 7,052,920 B2 | 5/2006 | Ushio |
| 7,059,268 B2 | 6/2006 | Russell |
| 7,067,034 B2 | 6/2006 | Bailey, III |
| 7,074,501 B2 | 7/2006 | Czeremuszkin |
| 7,098,453 B2 | 8/2006 | Ando |
| 7,109,070 B2 | 9/2006 | Behle |
| 7,112,352 B2 | 9/2006 | Schaepkens |
| 7,112,541 B2 | 9/2006 | Xia |
| 7,115,310 B2 | 10/2006 | Jacoud |
| 7,118,538 B2 | 10/2006 | Konrad |
| 7,119,908 B2 | 10/2006 | Nomoto |
| 7,121,135 B2 | 10/2006 | Moore |
| 7,130,373 B2 | 10/2006 | Omote |
| 7,150,299 B2 | 12/2006 | Hertzler |
| 7,160,292 B2 | 1/2007 | Moorman |
| 7,183,197 B2 | 2/2007 | Won |
| 7,186,242 B2 | 3/2007 | Gyure |
| 7,188,734 B2 | 3/2007 | Konrad |
| 7,189,290 B2 | 3/2007 | Hama |
| 7,193,724 B2 | 3/2007 | Isei |
| 7,198,685 B2 | 4/2007 | Hetzler |
| 7,206,074 B2 | 4/2007 | Fujimoto |
| 7,214,214 B2 | 5/2007 | Sudo |
| 7,244,381 B2 | 7/2007 | Chatard |
| 7,253,892 B2 | 8/2007 | Semersky |
| 7,286,242 B2 | 10/2007 | Kim |
| 7,288,293 B2 | 10/2007 | Koulik |
| 7,297,216 B2 | 11/2007 | Hetzler |
| 7,297,640 B2 | 11/2007 | Xie |
| 7,300,684 B2 | 11/2007 | Boardman |
| 7,303,789 B2 | 12/2007 | Saito |
| 7,303,790 B2 | 12/2007 | Delaunay |
| 7,306,852 B2 | 12/2007 | Komada |
| 7,332,227 B2 | 2/2008 | Hardman |
| 7,338,576 B2 | 3/2008 | Ono |
| 7,339,682 B2 | 3/2008 | Aiyer |
| 7,344,766 B1 | 3/2008 | Sorensen |
| 7,348,055 B2 | 3/2008 | Chappa |
| 7,348,192 B2 | 3/2008 | Mikami |
| 7,362,425 B2 | 4/2008 | Meeks |
| 7,381,469 B2 | 6/2008 | Moelle |
| 7,390,573 B2 | 6/2008 | Korevaar |
| 7,399,500 B2 | 7/2008 | Bicker |
| 7,405,008 B2 | 7/2008 | Domine |
| 7,409,313 B2 | 8/2008 | Ringermacher |
| 7,411,685 B2 | 8/2008 | Takashima |
| RE40,531 E | 10/2008 | Graff |
| 7,431,989 B2 | 10/2008 | Sakhrani |
| 7,438,783 B2 | 10/2008 | Miyata |
| 7,444,955 B2 | 11/2008 | Boardman |
| 7,455,892 B2 | 11/2008 | Goodwin |
| 7,480,363 B2 | 1/2009 | Lasiuk |
| 7,488,683 B2 | 2/2009 | Kobayashi |
| 7,494,941 B2 | 2/2009 | Kasahara |
| 7,507,378 B2 | 3/2009 | Reichenbach |
| 7,513,953 B1 | 4/2009 | Felts |
| 7,520,965 B2 | 4/2009 | Wei |
| 7,521,022 B2 | 4/2009 | Konrad |
| 7,534,615 B2 | 5/2009 | Havens |
| 7,534,733 B2 | 5/2009 | Bookbinder |
| RE40,787 E | 6/2009 | Martin |
| 7,541,069 B2 | 6/2009 | Tudhope |
| 7,547,297 B2 | 6/2009 | Brinkhues |
| 7,552,620 B2 | 6/2009 | DeRoos |
| 7,553,529 B2 | 6/2009 | Sakhrani |
| 7,555,934 B2 | 7/2009 | DeRoos |
| 7,569,035 B1 | 8/2009 | Wilmot |
| 7,579,056 B2 | 8/2009 | Brown |
| 7,582,868 B2 | 9/2009 | Jiang |
| 7,595,097 B2 | 9/2009 | Iacovangelo |
| 7,608,151 B2 | 10/2009 | Tudhope |
| 7,618,686 B2 | 11/2009 | Colpo |
| 7,624,622 B1 | 12/2009 | Mayer |
| 7,625,494 B2 | 12/2009 | Honda |
| 7,645,696 B1 | 1/2010 | Dulkin |
| 7,648,481 B2 | 1/2010 | Geiger |
| 7,682,816 B2 | 3/2010 | Kim |
| 7,691,308 B2 | 4/2010 | Brinkhues |
| 7,694,403 B2 | 4/2010 | Moulton |
| 7,704,683 B2 | 4/2010 | Wittenberg |
| 7,713,638 B2 | 5/2010 | Moelle |
| 7,736,689 B2 | 6/2010 | Chappa |
| 7,740,610 B2 | 6/2010 | Moh |
| 7,744,567 B2 | 6/2010 | Glowacki |
| 7,744,790 B2 | 6/2010 | Behle |
| 7,745,228 B2 | 6/2010 | Schwind |
| 7,745,547 B1 | 6/2010 | Auerbach |
| 7,749,202 B2 | 7/2010 | Miller |
| 7,749,914 B2 | 7/2010 | Honda |
| 7,754,302 B2 | 7/2010 | Yamaski |
| 7,766,882 B2 | 8/2010 | Sudo |
| 7,780,866 B2 | 8/2010 | Miller |
| 7,785,862 B2 | 8/2010 | Kim |
| 7,790,475 B2 | 9/2010 | Galbraith |
| 7,798,993 B2 | 9/2010 | Lim |
| 7,803,305 B2 | 9/2010 | Ahern |
| 7,807,242 B2 | 10/2010 | Soerensen |
| 7,815,922 B2 | 10/2010 | Chaney |
| 7,846,293 B2 | 12/2010 | Iwasaki |
| 7,854,889 B2 | 12/2010 | Perot |
| 7,867,366 B1 | 1/2011 | McFarland |
| 7,905,866 B2 | 3/2011 | Haider |
| 7,922,880 B1 | 4/2011 | Pradhan |
| 7,922,958 B2 | 4/2011 | D'Arrigo |
| 7,927,315 B2 | 4/2011 | Sudo |
| 7,931,955 B2 | 4/2011 | Behle |
| 7,932,678 B2 | 4/2011 | Madocks |

(56) References Cited

U.S. PATENT DOCUMENTS

| | | |
|---|---|---|
| 7,934,613 B2 | 5/2011 | Sudo |
| 7,943,205 B2 | 5/2011 | Schaepkens |
| 7,947,337 B2 | 5/2011 | Kuepper |
| 7,955,986 B2 | 6/2011 | Hoffman |
| 7,960,043 B2 | 6/2011 | Harris |
| 7,964,438 B2 | 6/2011 | Roca I Cabarrocas |
| 7,967,945 B2 | 6/2011 | Glukhoy |
| 7,975,646 B2 | 7/2011 | Rius |
| 7,985,188 B2 | 7/2011 | Felts |
| 8,002,754 B2 | 8/2011 | Kawamura |
| 8,025,915 B2 | 9/2011 | Haines |
| 8,038,858 B1 | 10/2011 | Bures |
| 8,039,524 B2 | 10/2011 | Chappa |
| 8,056,719 B2 | 11/2011 | Porret |
| 8,062,266 B2 | 11/2011 | McKinnon |
| 8,066,663 B2 | 11/2011 | Sudo |
| 8,066,854 B2 | 11/2011 | Storey |
| 8,070,917 B2 | 12/2011 | Tsukamoto |
| 8,075,995 B2 | 12/2011 | Zhao |
| 8,092,605 B2 | 1/2012 | Shannon |
| 8,101,246 B2 | 1/2012 | Fayet |
| 8,101,674 B2 | 1/2012 | Kawauchi |
| 8,105,294 B2 | 1/2012 | Araki |
| 8,197,452 B2 | 6/2012 | Harding |
| 8,227,025 B2 | 7/2012 | Lewis |
| 8,258,486 B2 | 9/2012 | Avnery |
| 8,268,410 B2 | 9/2012 | Moelle |
| 8,273,222 B2 | 9/2012 | Wei |
| 8,277,025 B2 | 10/2012 | Nakazawa et al. |
| 8,313,455 B2 | 11/2012 | DiGregorio |
| 8,323,166 B2 | 12/2012 | Haines |
| 8,389,958 B2 | 3/2013 | Vo-Dinh |
| 8,397,667 B2 | 3/2013 | Behle |
| 8,409,441 B2 | 4/2013 | Wilt |
| 8,418,650 B2 | 4/2013 | Goto |
| 8,435,605 B2 | 5/2013 | Aitken et al. |
| 8,475,886 B2 | 7/2013 | Chen et al. |
| 8,512,796 B2 | 8/2013 | Felts |
| 8,524,331 B2 | 9/2013 | Honda |
| 8,592,015 B2 | 11/2013 | Bicker |
| 8,603,638 B2 | 12/2013 | Liu |
| 8,618,509 B2 | 12/2013 | Vo-Dinh |
| 8,623,324 B2 | 1/2014 | Diwu |
| 8,633,034 B2 | 1/2014 | Trotter |
| 8,747,962 B2 | 6/2014 | Bicker |
| 8,802,603 B2 | 8/2014 | D'Souza |
| 8,816,022 B2 | 8/2014 | Zhao |
| 9,068,565 B2 | 6/2015 | Alarcon |
| 2001/0000279 A1 | 4/2001 | Daniels |
| 2001/0021356 A1 | 9/2001 | Konrad |
| 2001/0038894 A1 | 11/2001 | Komada |
| 2001/0042510 A1 | 11/2001 | Plester |
| 2001/0043997 A1 | 11/2001 | Uddin |
| 2002/0006487 A1 | 1/2002 | O'Connor |
| 2002/0007796 A1 | 1/2002 | Gorokhovsky |
| 2002/0070647 A1 | 6/2002 | Ginovker |
| 2002/0117114 A1 | 8/2002 | Ikenaga |
| 2002/0125900 A1 | 9/2002 | Savtchouk |
| 2002/0130674 A1 | 9/2002 | Lagowski |
| 2002/0141477 A1 | 10/2002 | Akahori |
| 2002/0153103 A1 | 10/2002 | Madocks |
| 2002/0155218 A1 | 10/2002 | Meyer |
| 2002/0170495 A1 | 11/2002 | Nakamura |
| 2002/0176947 A1 | 11/2002 | Darras |
| 2002/0182101 A1 | 12/2002 | Koulik |
| 2002/0185226 A1 | 12/2002 | Lea |
| 2002/0190207 A1 | 12/2002 | Levy |
| 2003/0010454 A1 | 1/2003 | Bailey, III |
| 2003/0013818 A1 | 1/2003 | Hakuta |
| 2003/0029837 A1 | 2/2003 | Trow |
| 2003/0031806 A1 | 2/2003 | Jinks |
| 2003/0046982 A1 | 3/2003 | Chartard |
| 2003/0102087 A1 | 6/2003 | Ito |
| 2003/0119193 A1 | 6/2003 | Hess |
| 2003/0159654 A1 | 8/2003 | Arnold |
| 2003/0215652 A1 | 11/2003 | O'Connor |
| 2003/0219547 A1 | 11/2003 | Arnold |
| 2003/0232150 A1 | 12/2003 | Arnold |
| 2004/0024371 A1 | 2/2004 | Plicchi |
| 2004/0039401 A1 | 2/2004 | Chow |
| 2004/0040372 A1 | 3/2004 | Plester |
| 2004/0045811 A1 | 3/2004 | Wang |
| 2004/0050744 A1 | 3/2004 | Hama |
| 2004/0055538 A1 | 3/2004 | Gorokhovsky |
| 2004/0071960 A1 | 4/2004 | Weber |
| 2004/0082917 A1 | 4/2004 | Hetzler |
| 2004/0084151 A1 | 5/2004 | Kim |
| 2004/0125913 A1 | 7/2004 | Larson |
| 2004/0135081 A1 | 7/2004 | Larson |
| 2004/0149225 A1 | 8/2004 | Weikart |
| 2004/0175961 A1 | 9/2004 | Olsen |
| 2004/0177676 A1 | 9/2004 | Moore |
| 2004/0195960 A1 | 10/2004 | Czeremuszkin |
| 2004/0206309 A1 | 10/2004 | Bera |
| 2004/0217081 A1 | 11/2004 | Konrad |
| 2004/0247948 A1 | 12/2004 | Behle |
| 2004/0267194 A1 | 12/2004 | Sano |
| 2005/0000962 A1 | 1/2005 | Crawford |
| 2005/0010175 A1 | 1/2005 | Beedon |
| 2005/0019503 A1 | 1/2005 | Komada |
| 2005/0037165 A1 | 2/2005 | Ahern |
| 2005/0039854 A1 | 2/2005 | Matsuyama |
| 2005/0045472 A1 | 3/2005 | Nagata |
| 2005/0057754 A1 | 3/2005 | Smith |
| 2005/0073323 A1 | 4/2005 | Kohno |
| 2005/0075611 A1 | 4/2005 | Hetzler |
| 2005/0075612 A1 | 4/2005 | Lee |
| 2005/0161149 A1 | 7/2005 | Yokota |
| 2005/0169803 A1 | 8/2005 | Betz |
| 2005/0190450 A1 | 9/2005 | Becker |
| 2005/0196629 A1 | 9/2005 | Bariatinsky |
| 2005/0199571 A1 | 9/2005 | Geisler |
| 2005/0206907 A1 | 9/2005 | Fujimoto |
| 2005/0211383 A1 | 9/2005 | Miyata |
| 2005/0223988 A1 | 10/2005 | Behle |
| 2005/0227002 A1 | 10/2005 | Lizenberg |
| 2005/0227022 A1 | 10/2005 | Domine |
| 2005/0229850 A1 | 10/2005 | Behle |
| 2005/0233077 A1 | 10/2005 | Lizenberg |
| 2005/0233091 A1 | 10/2005 | Kumar |
| 2005/0236346 A1 | 10/2005 | Whitney |
| 2005/0260504 A1 | 11/2005 | Becker |
| 2005/0284550 A1 | 12/2005 | Bicker |
| 2006/0005608 A1 | 1/2006 | Kitzhoffer |
| 2006/0013997 A1 | 1/2006 | Kuepper |
| 2006/0014309 A1 | 1/2006 | Sachdev |
| 2006/0024849 A1 | 2/2006 | Zhu |
| 2006/0042755 A1 | 3/2006 | Holmberg |
| 2006/0046006 A1 | 3/2006 | Bastion |
| 2006/0051252 A1 | 3/2006 | Yuan |
| 2006/0051520 A1 | 3/2006 | Behle |
| 2006/0076231 A1 | 4/2006 | Wei |
| 2006/0086320 A1 | 4/2006 | Lizenberg |
| 2006/0099340 A1 | 5/2006 | Behle |
| 2006/0121222 A1 | 6/2006 | Andrich |
| 2006/0121613 A1 | 6/2006 | Havens |
| 2006/0121623 A1 | 6/2006 | He |
| 2006/0127699 A1 | 6/2006 | Moelle |
| 2006/0135945 A1 | 6/2006 | Bankiewicz |
| 2006/0138326 A1 | 6/2006 | Jiang |
| 2006/0150909 A1 | 7/2006 | Behle |
| 2006/0169026 A1 | 8/2006 | Kage |
| 2006/0178627 A1 | 8/2006 | Geiger |
| 2006/0183345 A1 | 8/2006 | Nguyen |
| 2006/0192973 A1 | 8/2006 | Aiyer |
| 2006/0196419 A1 | 9/2006 | Tudhope |
| 2006/0198903 A1 | 9/2006 | Storey |
| 2006/0198965 A1 | 9/2006 | Tudhope |
| 2006/0200078 A1 | 9/2006 | Konrad |
| 2006/0200084 A1 | 9/2006 | Ito |
| 2006/0210425 A1 | 9/2006 | Mirkarimi |
| 2006/0228497 A1 | 10/2006 | Kumar |
| 2006/0260360 A1 | 11/2006 | Dick |
| 2007/0003441 A1 | 1/2007 | Wohleb |

(56) References Cited

U.S. PATENT DOCUMENTS

| | | |
|---|---|---|
| 2007/0009673 A1 | 1/2007 | Fukazawa et al. |
| 2007/0017870 A1 | 1/2007 | Belov |
| 2007/0048456 A1 | 3/2007 | Keshner |
| 2007/0049048 A1 | 3/2007 | Rauf |
| 2007/0051629 A1 | 3/2007 | Donlik |
| 2007/0065680 A1 | 3/2007 | Schultheis |
| 2007/0076833 A1 | 4/2007 | Becker |
| 2007/0102344 A1 | 5/2007 | Konrad |
| 2007/0123920 A1 | 5/2007 | Inokuti |
| 2007/0148326 A1 | 6/2007 | Hatings |
| 2007/0166187 A1 | 7/2007 | Song |
| 2007/0184657 A1 | 8/2007 | Iijima |
| 2007/0187229 A1 | 8/2007 | Aksenov |
| 2007/0187280 A1 | 8/2007 | Haines |
| 2007/0205096 A1 | 9/2007 | Nagashima |
| 2007/0215009 A1 | 9/2007 | Shimazu |
| 2007/0215046 A1 | 9/2007 | Lupke |
| 2007/0218265 A1 | 9/2007 | Harris |
| 2007/0224236 A1 | 9/2007 | Boden |
| 2007/0231655 A1 | 10/2007 | Ha |
| 2007/0232066 A1 | 10/2007 | Bicker |
| 2007/0235890 A1 | 10/2007 | Lewis |
| 2007/0243618 A1 | 10/2007 | Hatchett |
| 2007/0251458 A1 | 11/2007 | Mund |
| 2007/0258894 A1 | 11/2007 | Melker et al. |
| 2007/0259184 A1 | 11/2007 | Martin |
| 2007/0281108 A1 | 12/2007 | Weikart |
| 2007/0281117 A1 | 12/2007 | Kaplan |
| 2007/0287950 A1 | 12/2007 | Kjeken |
| 2007/0287954 A1 | 12/2007 | Zhao |
| 2007/0298189 A1 | 12/2007 | Straemke |
| 2008/0011232 A1 | 1/2008 | Ruis |
| 2008/0017113 A1 | 1/2008 | Goto |
| 2008/0023414 A1 | 1/2008 | Konrad |
| 2008/0027400 A1 | 1/2008 | Harding |
| 2008/0045880 A1 | 2/2008 | Kjeken |
| 2008/0050567 A1 | 2/2008 | Kawashima |
| 2008/0050932 A1 | 2/2008 | Lakshmanan |
| 2008/0069970 A1 | 3/2008 | Wu |
| 2008/0071228 A1 | 3/2008 | Wu |
| 2008/0081184 A1 | 4/2008 | Kubo |
| 2008/0090039 A1 | 4/2008 | Klein |
| 2008/0093245 A1 | 4/2008 | Periasamy |
| 2008/0102206 A1 | 5/2008 | Wagner |
| 2008/0109017 A1 | 5/2008 | Herweck |
| 2008/0110852 A1 | 5/2008 | Kuroda |
| 2008/0113109 A1 | 5/2008 | Moelle |
| 2008/0118734 A1 | 5/2008 | Goodwin |
| 2008/0131628 A1 | 6/2008 | Abensour |
| 2008/0131638 A1 | 6/2008 | Hutton |
| 2008/0139003 A1 | 6/2008 | Pirzada |
| 2008/0145271 A1 | 6/2008 | Kidambi |
| 2008/0187681 A1 | 8/2008 | Hofrichter |
| 2008/0195059 A1 | 8/2008 | Sudo |
| 2008/0202414 A1 | 8/2008 | Yan |
| 2008/0206477 A1 | 8/2008 | Rius |
| 2008/0210550 A1 | 9/2008 | Walther et al. |
| 2008/0220164 A1 | 9/2008 | Bauch |
| 2008/0223815 A1 | 9/2008 | Konrad |
| 2008/0233355 A1 | 9/2008 | Henze |
| 2008/0260966 A1 | 10/2008 | Hanawa |
| 2008/0268252 A1 | 10/2008 | Garces |
| 2008/0277332 A1 | 11/2008 | Liu |
| 2008/0289957 A1 | 11/2008 | Takigawa |
| 2008/0292806 A1 | 11/2008 | Wei |
| 2008/0295772 A1 | 12/2008 | Park |
| 2008/0303131 A1 | 12/2008 | Mcelerea |
| 2008/0312607 A1 | 12/2008 | Delmotte |
| 2008/0314318 A1 | 12/2008 | Han |
| 2009/0004091 A1 | 1/2009 | Kang |
| 2009/0004363 A1 | 1/2009 | Keshner |
| 2009/0017217 A1 | 1/2009 | Hass |
| 2009/0022981 A1 | 1/2009 | Yoshida |
| 2009/0029402 A1 | 1/2009 | Papkovsky |
| 2009/0031953 A1 | 2/2009 | Ingle |
| 2009/0032393 A1 | 2/2009 | Madocks |
| 2009/0039240 A1 | 2/2009 | Van Nijnatten |
| 2009/0053491 A1 | 2/2009 | Loboda |
| 2009/0061237 A1 | 3/2009 | Gates |
| 2009/0065485 A1 | 3/2009 | O'Neill |
| 2009/0069790 A1 | 3/2009 | Yokley |
| 2009/0081797 A1 | 3/2009 | Fadeev |
| 2009/0099512 A1 | 4/2009 | Digregorio |
| 2009/0104392 A1 | 4/2009 | Takada |
| 2009/0117268 A1 | 5/2009 | Lewis |
| 2009/0117389 A1 | 5/2009 | Amberg-Schwab |
| 2009/0122832 A1 | 5/2009 | Feist |
| 2009/0134884 A1 | 5/2009 | Bosselmann |
| 2009/0137966 A1 | 5/2009 | Rueckert |
| 2009/0142227 A1 | 6/2009 | Fuchs |
| 2009/0142514 A1 | 6/2009 | O'Neill |
| 2009/0147719 A1 | 6/2009 | Kang |
| 2009/0149816 A1 | 6/2009 | Hetzler |
| 2009/0155490 A1 | 6/2009 | Bicker |
| 2009/0162571 A1 | 6/2009 | Haines |
| 2009/0166312 A1 | 7/2009 | Giraud |
| 2009/0176031 A1 | 7/2009 | Armellin |
| 2009/0214801 A1 | 8/2009 | Higashi |
| 2009/0220948 A1 | 9/2009 | Oviso et al. |
| 2009/0263668 A1 | 10/2009 | David |
| 2009/0274851 A1 | 11/2009 | Goundar |
| 2009/0280268 A1 | 11/2009 | Glukhoy |
| 2009/0297730 A1 | 12/2009 | Glukhoy |
| 2009/0306595 A1 | 12/2009 | Shih |
| 2009/0326517 A1 | 12/2009 | Bork |
| 2010/0021998 A1 | 1/2010 | Sanyal |
| 2010/0028238 A1 | 2/2010 | Maschwitz |
| 2010/0034985 A1 | 2/2010 | Krueger |
| 2010/0042055 A1 | 2/2010 | Sudo |
| 2010/0075077 A1 | 3/2010 | Bicker |
| 2010/0086808 A1 | 4/2010 | Nagata |
| 2010/0089097 A1 | 4/2010 | Brack |
| 2010/0104770 A1 | 4/2010 | Goundar |
| 2010/0105208 A1 | 4/2010 | Winniczek |
| 2010/0132762 A1 | 6/2010 | Graham, Jr. |
| 2010/0145284 A1 | 6/2010 | Togashi |
| 2010/0174239 A1 | 7/2010 | Yodfat |
| 2010/0174245 A1 | 7/2010 | Halverson |
| 2010/0178490 A1 | 7/2010 | Cerny |
| 2010/0185157 A1 | 7/2010 | Kawamura |
| 2010/0186740 A1 | 7/2010 | Lewis |
| 2010/0190036 A1 | 7/2010 | Komvopoulos |
| 2010/0193461 A1 | 8/2010 | Boutroy |
| 2010/0198554 A1 | 8/2010 | Skliar |
| 2010/0204648 A1 | 8/2010 | Stout |
| 2010/0230281 A1 | 9/2010 | Park |
| 2010/0231194 A1 | 9/2010 | Bauch |
| 2010/0237545 A1 | 9/2010 | Haury |
| 2010/0264139 A1 | 10/2010 | Kawachi |
| 2010/0273261 A1 | 10/2010 | Chen |
| 2010/0275847 A1 | 11/2010 | Yamasaki |
| 2010/0279397 A1 | 11/2010 | Crawford |
| 2010/0298738 A1 | 11/2010 | Felts |
| 2010/0298779 A1 | 11/2010 | Hetzler |
| 2011/0037159 A1 | 2/2011 | Mcelrea |
| 2011/0046570 A1 | 2/2011 | Stout |
| 2011/0056912 A1 | 3/2011 | Magsuyama |
| 2011/0062047 A1 | 3/2011 | Haines |
| 2011/0065798 A1 | 3/2011 | Hoang |
| 2011/0079582 A1 | 4/2011 | Yonesu |
| 2011/0093056 A1 | 4/2011 | Kaplan |
| 2011/0111132 A1 | 5/2011 | Wei |
| 2011/0117202 A1 | 5/2011 | Bourke, Jr. |
| 2011/0117288 A1 | 5/2011 | Honda |
| 2011/0137263 A1 | 6/2011 | Ashmead |
| 2011/0152820 A1 | 6/2011 | Chattaraj |
| 2011/0159101 A1 | 6/2011 | Kurdyumov et al. |
| 2011/0160662 A1 | 6/2011 | Stout |
| 2011/0160663 A1 | 6/2011 | Stout |
| 2011/0174220 A1 | 7/2011 | Laure |
| 2011/0186537 A1 | 8/2011 | Rodriguez San Juan |
| 2011/0220490 A1 | 9/2011 | Wei |
| 2011/0252899 A1* | 10/2011 | Felts .................... C23C 16/045 73/865.8 |

(56) References Cited

U.S. PATENT DOCUMENTS

| | | |
|---|---|---|
| 2011/0253674 A1 | 10/2011 | Chung |
| 2011/0313363 A1 | 12/2011 | D'Souza |
| 2011/0319758 A1 | 12/2011 | Wang |
| 2011/0319813 A1 | 12/2011 | Kamen |
| 2012/0003497 A1 | 1/2012 | Handy |
| 2012/0004339 A1 | 1/2012 | Chappa |
| 2012/0021136 A1 | 1/2012 | Dzengeleski |
| 2012/0031070 A1 | 2/2012 | Slough |
| 2012/0035543 A1 | 2/2012 | Kamen |
| 2012/0052123 A9 | 3/2012 | Kurdyumov et al. |
| 2012/0053530 A1 | 3/2012 | Zhao |
| 2012/0058351 A1 | 3/2012 | Zhao |
| 2012/0065612 A1 | 3/2012 | Stout |
| 2012/0097527 A1 | 4/2012 | Kodaira |
| 2012/0097870 A1 | 4/2012 | Leray |
| 2012/0108058 A1 | 5/2012 | Ha |
| 2012/0109076 A1 | 5/2012 | Kawamura |
| 2012/0123345 A1 | 5/2012 | Felts |
| 2012/0141913 A1 | 6/2012 | Lee |
| 2012/0143148 A1 | 6/2012 | Zhao |
| 2012/0149871 A1 | 6/2012 | Saxena |
| 2012/0171386 A1 | 7/2012 | Bicker |
| 2012/0175384 A1 | 7/2012 | Greter |
| 2012/0183954 A1 | 7/2012 | Diwu |
| 2012/0205374 A1 | 8/2012 | Klumpen |
| 2012/0231182 A1 | 9/2012 | Stevens |
| 2012/0234720 A1 | 9/2012 | Digregorio |
| 2012/0252709 A1 | 10/2012 | Felts |
| 2013/0041241 A1 | 2/2013 | Felts |
| 2013/0046375 A1 | 2/2013 | Chen |
| 2013/0057677 A1 | 3/2013 | Weil |
| 2013/0072025 A1 | 3/2013 | Singh |
| 2013/0081953 A1 | 4/2013 | Bruna et al. |
| 2013/0190695 A1 | 7/2013 | Wu |
| 2013/0209704 A1 | 8/2013 | Krueger |
| 2013/0264303 A1 | 10/2013 | Andersen |
| 2013/0296235 A1 | 11/2013 | Alarcon |
| 2014/0010969 A1 | 1/2014 | Bicker |
| 2014/0052076 A1 | 2/2014 | Zhao |
| 2014/0054803 A1 | 2/2014 | Chen |
| 2014/0099455 A1 | 4/2014 | Stanley |
| 2014/0110297 A1 | 4/2014 | Trotter |
| 2014/0135708 A1 | 5/2014 | Lewis |
| 2014/0147654 A1 | 5/2014 | Walther |
| 2014/0151320 A1 | 6/2014 | Chang |
| 2014/0151370 A1 | 6/2014 | Chang |
| 2014/0187666 A1 | 7/2014 | Aizenberg |
| 2014/0190846 A1 | 7/2014 | Belt |
| 2014/0221934 A1 | 8/2014 | Janvier |
| 2014/0251856 A1 | 9/2014 | Larsson |
| 2014/0251859 A1 | 9/2014 | Weikart |
| 2014/0305830 A1 | 10/2014 | Bicker |
| 2015/0165125 A1 | 6/2015 | Foucher |
| 2015/0224263 A1 | 8/2015 | Dugand |

FOREIGN PATENT DOCUMENTS

| | | |
|---|---|---|
| CA | 2277679 A1 | 7/1997 |
| CA | 2355681 | 7/2000 |
| CA | 2571380 A1 | 7/2006 |
| CA | 2718253 | 9/2009 |
| CA | 2268719 C | 8/2010 |
| CN | 2546041 Y | 4/2003 |
| CN | 1711310 A | 12/2005 |
| CN | 2766863 Y | 3/2006 |
| CN | 1898172 A | 1/2007 |
| CN | 201002786 Y | 1/2008 |
| CN | 101147813 A | 3/2008 |
| CN | 201056331 Y | 5/2008 |
| CN | 102581274 A | 7/2012 |
| DE | 1147836 | 4/1969 |
| DE | 1147838 | 4/1969 |
| DE | 3908418 A1 | 9/1990 |
| DE | 4214401 C1 | 3/1993 |
| DE | 4316349 A1 | 11/1994 |
| DE | 4438359 | 5/1996 |
| DE | 19707645 A1 | 8/1998 |
| DE | 19830794 A1 | 1/2000 |
| DE | 19912737 A1 | 6/2000 |
| DE | 10010831 A1 | 9/2001 |
| DE | 10154404 C1 | 6/2003 |
| DE | 10201110 A1 | 10/2003 |
| DE | 10353540 A1 | 5/2004 |
| DE | 102004017236 A1 | 10/2005 |
| DE | 102006061585 A1 | 2/2008 |
| DE | 102008023027 A1 | 11/2009 |
| EP | 0121340 A2 | 10/1984 |
| EP | 0251812 A2 | 1/1988 |
| EP | 0275965 A2 | 7/1988 |
| EP | 0284867 A2 | 10/1988 |
| EP | 0306307 | 3/1989 |
| EP | 0329041 A2 | 8/1989 |
| EP | 0343017 A2 | 11/1989 |
| EP | 0396919 A2 | 11/1990 |
| EP | 0482613 A1 | 10/1991 |
| EP | 0484746 A2 | 10/1991 |
| EP | 0495447 A1 | 7/1992 |
| EP | 0520519 A1 | 12/1992 |
| EP | 0535810 A1 | 4/1993 |
| EP | 0375778 B1 | 9/1993 |
| EP | 0571116 A1 | 11/1993 |
| EP | 0580094 A1 | 1/1994 |
| EP | 0603717 A2 | 6/1994 |
| EP | 0619178 | 10/1994 |
| EP | 0645470 A1 | 3/1995 |
| EP | 0697378 A2 | 2/1996 |
| EP | 0709485 B1 | 5/1996 |
| EP | 0719877 A1 | 7/1996 |
| EP | 0728676 A1 | 8/1996 |
| EP | 0787824 A2 | 8/1997 |
| EP | 0787828 A2 | 8/1997 |
| EP | 0814114 A1 | 12/1997 |
| EP | 0833366 A2 | 4/1998 |
| EP | 0879611 A2 | 11/1998 |
| EP | 0940183 A2 | 9/1999 |
| EP | 0962229 A2 | 12/1999 |
| EP | 0992610 A2 | 4/2000 |
| EP | 1119034 A1 | 7/2001 |
| EP | 0954272 B1 | 3/2002 |
| EP | 1245694 A1 | 10/2002 |
| EP | 1388594 B1 | 1/2003 |
| EP | 1317937 A1 | 6/2003 |
| EP | 1365043 A1 | 11/2003 |
| EP | 1367145 | 12/2003 |
| EP | 1388593 A1 | 2/2004 |
| EP | 1439241 A2 | 7/2004 |
| EP | 1447459 A2 | 8/2004 |
| EP | 1990639 A1 | 2/2005 |
| EP | 1510595 A1 | 3/2005 |
| EP | 1522403 A2 | 4/2005 |
| EP | 1901067 A2 | 8/2005 |
| EP | 1507894 | 12/2005 |
| EP | 1653192 A1 | 5/2006 |
| EP | 1810758 A1 | 7/2007 |
| EP | 1356260 B1 | 12/2007 |
| EP | 1870117 A2 | 12/2007 |
| EP | 1881088 A1 | 1/2008 |
| EP | 1507887 | 7/2008 |
| EP | 1415018 | 10/2008 |
| EP | 2199264 A1 | 11/2009 |
| EP | 1388594 B1 | 1/2010 |
| EP | 2178109 A1 | 4/2010 |
| EP | 1507895 | 7/2010 |
| EP | 2218465 A1 | 8/2010 |
| EP | 2243751 A1 | 10/2010 |
| EP | 2251671 | 11/2010 |
| EP | 2261185 | 12/2010 |
| EP | 2369038 A2 | 9/2011 |
| EP | 1960279 B1 | 10/2011 |
| EP | 2602354 A1 | 6/2013 |
| EP | 2639330 A1 | 9/2013 |
| GB | 752822 | 7/1956 |
| GB | 1363762 | 8/1974 |
| GB | 1513426 A | 6/1978 |

(56) References Cited

FOREIGN PATENT DOCUMENTS

| | | |
|---|---|---|
| GB | 1566251 | 4/1980 |
| GB | 2210826 A | 6/1989 |
| GB | 2231197 A | 11/1990 |
| GB | 2246794 A | 2/1992 |
| GB | 2246795 A | 2/1992 |
| GB | 2387964 A | 10/2003 |
| JP | 56027330 A | 3/1981 |
| JP | 58154602 A | 9/1983 |
| JP | 59087307 A | 5/1984 |
| JP | 59154029 | 9/1984 |
| JP | S61183462 A | 8/1986 |
| JP | S62180069 A | 8/1987 |
| JP | S62290866 A | 12/1987 |
| JP | 63124521 A2 | 5/1988 |
| JP | 1023105 A | 1/1989 |
| JP | H01225775 A | 9/1989 |
| JP | 1279745 | 11/1989 |
| JP | 2501490 | 5/1990 |
| JP | 3183759 A2 | 8/1991 |
| JP | H03260065 A | 11/1991 |
| JP | H03271374 A | 12/1991 |
| JP | 4000373 A | 1/1992 |
| JP | 4000374 A | 1/1992 |
| JP | 4000375 A | 1/1992 |
| JP | 4014440 A | 1/1992 |
| JP | H04124273 A | 4/1992 |
| JP | H0578844 A | 3/1993 |
| JP | 05-006688 A | 4/1993 |
| JP | H05263223 A | 10/1993 |
| JP | 6010132 A | 1/1994 |
| JP | 6289401 | 10/1994 |
| JP | 7041579 A | 2/1995 |
| JP | 7068614 A | 3/1995 |
| JP | 7126419 A | 5/1995 |
| JP | 7-304127 | 11/1995 |
| JP | 8025244 A | 1/1996 |
| JP | 8084773 A | 4/1996 |
| JP | H08296038 A | 11/1996 |
| JP | 9005038 A | 1/1997 |
| JP | 10008254 A | 1/1998 |
| JP | 10-130844 | 5/1998 |
| JP | 11-108833 A | 4/1999 |
| JP | 11106920 | 4/1999 |
| JP | H11256331 A | 9/1999 |
| JP | 11344316 A | 12/1999 |
| JP | 2000064040 A | 2/2000 |
| JP | 2000109076 A | 4/2000 |
| JP | 2001033398 A | 2/2001 |
| JP | 2001231841 A | 8/2001 |
| JP | 2002177364 A | 6/2002 |
| JP | 2002206167 A | 7/2002 |
| JP | 2002371364 A | 12/2002 |
| JP | 2003171771 A | 6/2003 |
| JP | 2003-268550 A | 9/2003 |
| JP | 2003305121 A | 10/2003 |
| JP | 2004002928 A | 1/2004 |
| JP | 2004008509 A | 1/2004 |
| JP | 2004043789 A | 2/2004 |
| JP | 2004100036 A | 4/2004 |
| JP | 2004156444 A | 6/2004 |
| JP | 2004168359 A | 6/2004 |
| JP | 2004169087 A | 6/2004 |
| JP | 2004203682 A | 7/2004 |
| JP | 2004-253683 A | 9/2004 |
| JP | 2004307935 A | 11/2004 |
| JP | 2005035597 A | 2/2005 |
| JP | 2005043285 A | 2/2005 |
| JP | 2005132416 A | 5/2005 |
| JP | 2005160888 A | 6/2005 |
| JP | 2005-200044 | 7/2005 |
| JP | 2005200044 A | 7/2005 |
| JP | 2005-241524 A | 9/2005 |
| JP | 2005-290560 A | 10/2005 |
| JP | 2005271997 A | 10/2005 |
| JP | 2005290561 A | 10/2005 |
| JP | 2006-064416 A | 3/2006 |
| JP | 2006111967 A | 4/2006 |
| JP | 2006160268 A | 6/2006 |
| JP | 2006-224992 A | 8/2006 |
| JP | 2006249577 A | 9/2006 |
| JP | 2007050898 A | 3/2007 |
| JP | 2007231386 A | 9/2007 |
| JP | 2007246974 A | 9/2007 |
| JP | 2008-132766 A | 6/2008 |
| JP | 2008174793 A | 7/2008 |
| JP | 2009-062620 A | 3/2009 |
| JP | 2009062620 A | 3/2009 |
| JP | 2009079298 A | 4/2009 |
| JP | 2009084203 A | 4/2009 |
| JP | 2009185330 A | 8/2009 |
| JP | 2010155134 A | 7/2010 |
| JP | 2012210315 A | 11/2012 |
| JP | 5362941 B2 | 12/2013 |
| KR | 10-2005-0100367 A | 10/2005 |
| KR | 10-0685594 B1 | 2/2007 |
| TW | 200703536 A | 1/2007 |
| WO | WO9324243 A1 | 12/1993 |
| WO | WO9400247 A1 | 1/1994 |
| WO | WO9426497 A1 | 11/1994 |
| WO | WO95/24275 | 9/1995 |
| WO | WO199624392 A1 | 8/1996 |
| WO | WO97/11482 | 3/1997 |
| WO | WO97/13802 | 4/1997 |
| WO | WO98-27926 | 7/1998 |
| WO | WO98/45871 | 10/1998 |
| WO | WO9917334 A1 | 4/1999 |
| WO | WO99/41425 | 8/1999 |
| WO | WO99/50471 | 10/1999 |
| WO | WO0038566 A2 | 7/2000 |
| WO | WO0104668 A1 | 1/2001 |
| WO | WO0125788 | 4/2001 |
| WO | WO0154816 A1 | 8/2001 |
| WO | WO0156706 A1 | 8/2001 |
| WO | WO0170403 A1 | 9/2001 |
| WO | WO02/43116 A2 | 5/2002 |
| WO | WO0249925 A1 | 6/2002 |
| WO | WO02/056333 A1 | 7/2002 |
| WO | WO02072914 | 9/2002 |
| WO | WO03033426 | 9/2002 |
| WO | WO02076709 A1 | 10/2002 |
| WO | WO03014415 A1 | 2/2003 |
| WO | WO03038143 | 5/2003 |
| WO | WO03040649 A1 | 5/2003 |
| WO | WO03044240 A1 | 5/2003 |
| WO | WO2005035147 A1 | 4/2005 |
| WO | WO2005/052555 A1 | 6/2005 |
| WO | WO2005051525 A1 | 6/2005 |
| WO | WO2005103605 A1 | 11/2005 |
| WO | WO2006012881 A1 | 2/2006 |
| WO | WO2006027568 A1 | 3/2006 |
| WO | WO2006029743 A1 | 3/2006 |
| WO | WO2006044254 A1 | 4/2006 |
| WO | WO2006/048650 | 5/2006 |
| WO | WO2006048276 | 5/2006 |
| WO | WO2006048277 A1 | 5/2006 |
| WO | WO2006069774 A1 | 7/2006 |
| WO | WO2006135755 A2 | 12/2006 |
| WO | WO2007028061 A2 | 3/2007 |
| WO | WO2007035741 A2 | 3/2007 |
| WO | WO2007036544 A1 | 4/2007 |
| WO | WO2007/081814 | 7/2007 |
| WO | WO2007/089216 A1 | 8/2007 |
| WO | WO2007112328 A2 | 10/2007 |
| WO | WO2007120507 A2 | 10/2007 |
| WO | WO2007133378 A1 | 11/2007 |
| WO | WO2007134347 A2 | 11/2007 |
| WO | WO2008014438 A1 | 1/2008 |
| WO | WO2008024566 A2 | 2/2008 |
| WO | WO2008040531 A1 | 4/2008 |
| WO | WO2008047541 A1 | 4/2008 |
| WO | WO2008067574 A1 | 6/2008 |
| WO | WO2008071458 A1 | 6/2008 |
| WO | WO2008093335 A2 | 8/2008 |
| WO | 2008/121478 A2 | 10/2008 |

(56) References Cited

FOREIGN PATENT DOCUMENTS

| WO | WO2009/015862 A1 | 2/2009 |
|---|---|---|
| WO | WO2009020550 A2 | 2/2009 |
| WO | WO2009021257 A1 | 2/2009 |
| WO | WO2009030974 | 3/2009 |
| WO | WO2009030975 A1 | 3/2009 |
| WO | WO2009030976 A1 | 3/2009 |
| WO | WO2009031838 A1 | 3/2009 |
| WO | WO2009040109 | 4/2009 |
| WO | WO2009053947 A2 | 4/2009 |
| WO | WO2009112053 A1 | 9/2009 |
| WO | WO2009117032 | 9/2009 |
| WO | WO2009118361 A1 | 10/2009 |
| WO | WO2009158613 | 12/2009 |
| WO | WO2010047825 A1 | 4/2010 |
| WO | WO2010095011 A1 | 8/2010 |
| WO | WO2010/132579 | 11/2010 |
| WO | WO2010/132581 | 11/2010 |
| WO | WO2010/132584 | 11/2010 |
| WO | WO2010/132585 | 11/2010 |
| WO | WO2010/132589 | 11/2010 |
| WO | WO2010/132591 | 11/2010 |
| WO | WO2010034004 A1 | 11/2010 |
| WO | WO2010132579 A2 | 11/2010 |
| WO | WO2011029628 | 3/2011 |
| WO | WO2011007055 A1 | 6/2011 |
| WO | WO2011080543 A1 | 7/2011 |
| WO | WO2011082296 A1 | 7/2011 |
| WO | WO2011090717 A1 | 7/2011 |
| WO | WO2011/143329 | 11/2011 |
| WO | WO2011/143509 | 11/2011 |
| WO | WO2011/143509 A1 | 11/2011 |
| WO | WO2011137437 | 11/2011 |
| WO | WO2011143329 | 11/2011 |
| WO | WO2011159975 A1 | 12/2011 |
| WO | WO2012003221 | 1/2012 |
| WO | WO2012009653 | 1/2012 |
| WO | WO2013045671 A1 | 4/2013 |
| WO | WO2013/071138 | 5/2013 |
| WO | WO2013/071138 A1 | 5/2013 |
| WO | WO2013/170044 | 11/2013 |
| WO | WO2013/170052 | 11/2013 |
| WO | WO2014/008138 | 1/2014 |
| WO | WO2014/059012 | 4/2014 |
| WO | WO2014/071061 | 5/2014 |
| WO | WO2014/078666 | 5/2014 |
| WO | WO2014/085346 | 6/2014 |
| WO | WO2014/085348 | 6/2014 |
| WO | WO2014/134577 | 9/2014 |
| WO | WO2014/144926 | 9/2014 |
| WO | WO2014/164928 | 10/2014 |

OTHER PUBLICATIONS

PCT, Written Opinion of the International Preliminary Examining Authority, in International application No. PCT/US2013/071750, dated Jan. 20, 2015 (9 pages).

PCT, Written Opinion of the International Preliminary Examining Authority, in International application No. PCT/US2013/064121, dated Nov. 21, 2014 (7 pages).

Japanese Patent Office, Decision of Rejection in Application No. 2012-510983, dated Jan. 20, 2015 (4 pages).

Australian Government, IP Australia, Patent Examination Report No. 1, in Application No. 2010249033, dated Dec. 19, 2014 (7 pages).

Australian Government, IP Australia, Patent Examination Report No. 1, in Application No. 2011252925, dated Dec. 2, 2014 (3 pages).

Reh, et al., Evaluation of stationary phases for 2-dimensional HPLC of Proteins—Validation of commercial RP-columns, Published by Elsevier B.V., 2000.

Allison, H.L., The Real Markets for Transparent Barrier Films, 37th Annual Technical Conference Proceedings, 1994, ISBN 1-878068-13-X, pp. 458.

Bailey, R. et al., Thin-Film Multilayer Capacitors Using Pyrolytically Deposited Silicon Dioxide, IEEE Transactions on Parts, Hybrids, and Packaging, vol. PHP-12, No. 4, Dec. 1976, pp. 361-364.

Banks, B.A., et al., Fluoropolymer Filled SiO2 Coatings; Properties and Potential Applications, Society of Vacuum Coaters, 35th Annual Technical Conference Proceedings, 1992, ISBN 1-878068-11-3, pp. 89-93.

Baouchi, W., X-Ray Photoelectron Spectroscopy Study of Sodium Ion Migration through Thin Films of SiO2 Deposited on Sodalime Glass, 37th Annual Technical Conference Proceedings, 1994, ISBN 1-878068-13-X, pp. 419-422.

Boebel, F. et al., Simultaneous In Situ Measurement of Film Thickness and Temperature by Using Multiple Wavelengths Pyrometric Interferometry (MWPI), IEEE Transaction on Semiconductor Manufacturing, vol. 6, No. 2, May 1993, pp. 112-118.

Bush, V. et al., The Evolution of Evacuated Blood Collection Tubes, BD Diagnostics—Preanalytical Systems Newsletter, vol. 19, No. 1, 2009.

Chahroudi, D., Deposition Technology for Glass Barriers, 33rd Annual Technical Conference Proceedings, 1990, ISBN 1-878068-09-1, pp. 212-220.

Chahroudi, D., et al., Transparent Glass Barrier Coatings for Flexible Film Packaging, Society of Vacuum Coaters, 34th Annual Technical Conference Proceedings, 1991, ISBN 1-878068-10-5, pp. 130-133.

Chahroudi, D., Glassy Barriers from Electron Beam Web Coaters, 32nd Annual Technical Conference Proceedings, 1989, pp. 29-39.

Czeremuszkin, G. et al., Ultrathin Silicon-Compound Barrier Coatings for Polymeric Packaging Materials: An Industrial Perspective, Plasmas and Polymers, vol. 6, Nos. 1/2, Jun. 2001, pp. 107-120.

Ebihara, K. et al., Application of the Dielectric Barrier Discharge to Detect Defects in a Teflon Coated Metal Surface, 2003 J. Phys. D: Appl. Phys. 36 2883-2886, doi: 10.108810022-3727/36123/003, IOP Electronic Journals, http://www.iop.org/EJ/abstract/0022-3727/36/23/003, printed Jul. 14, 2009.

Egitto, F.D., et al., Plasma Modification of Polymer Surfaces, Society of Vacuum Coaters, 36th Annual Technical Conference Proceedings, 1993, ISBN 1-878068-12-1, pp. 10-21.

Erlat, A.G. et al., SIOx Gas Barrier Coatings on Polymer Substrates: Morphology and Gas Transport Considerations, ACS Publications, Journal of Physical Chemistry, published Jul. 2, 1999, http://pubs.acs.org/doi/abs/10.1021/jp990737e, printed Jul. 14, 2009.

Fayet, P., et al., Commercialism of Plasma Deposited Barrier Coatings for Liquid Food Packaging, 37th Annual Technical Conference Proceedings, 1995, ISBN 1-878068-13-X, pp. 15-16.

Felts, J., Hollow Cathode Based Multi-Component Depositions, Vacuum Technology & Coating, Mar. 2004, pp. 48-55.

Felts, J.T., Thickness Effects on Thin Film Gas Barriers: Silicon-Based Coatings, Society of Vacuum Coaters, 34th Annual Technical Conference Proceedings, 1991, ISBN 1-878068-10-5, pp. 99-104.

Felts, J.T., Transparent Barrier Coatings Update: Flexible Substrates, Society of Vacuum Coaters, 36th Annual Technical Conference Proceedings, 1993, ISBN 1-878068-12-1, pp. 324-331.

Felts, J.T., Transparent Gas Barrier Technologies, 33rd Annual Technical Conference Proceedings, 1990, ISBN 1-878068-09-1, pp. 184-193.

Finson, E., et al., Transparent SiO2 Barrier Coatings: Conversion and Production Status, 37th Annual Technical Conference Proceedings, 1994, ISBN 1-878068-13-X, pp. 139-143.

Flaherty, T. et al., Application of Spectral Reflectivity to the Measurement of Thin-Film Thickness, Opto-Ireland 2002: Optics and Photonics Technologies and Applications, Proceedings of SPIE vol. 4876, 2003, pp. 976-983.

Hora, R., et al., Plasma Polymerization: A New Technology for Functional Coatings on Plastics, 36th Annual Technical Conference Proceedings, 1993, ISBN 1-878068-12-1, pp. 51-55.

Izu, M., et al., High Performance Clear CoatTM Barrier Film, 36th Annual Technical Conference Proceedings, 1993, ISBN 1-878068-12-1, pp. 333-340.

Jost, S., Plasma Polymerized Organosilicon Thin Films on Reflective Coatings, 33rd Annual Technical Conference Proceedings, 1990, ISBN 1-878068-09-1, pp. 344-346.

(56) References Cited

OTHER PUBLICATIONS

Kaganowicz, G., et al., Plasma-Deposited Coatings—Properties and Applications, 23rd Annual Technical Conference Proceedings, 1980, pp. 24-30.

Kamineni, V. et al., Thickness Measurement of Thin Metal Films by Optical Metrology, College of Nanoscale Science and Engineering, University of Albany, Albany, NY, (2006).

Klemberg-Sapieha, J.E., et al., Transparent Gas Barrier Coatings Produced by Dual Frequency PECVD, 36th Annual Technical Conference Proceedings, 1993, ISBN 1-878068-12-1, pp. 445-449.

Krug, T., et al., New Developments in Transparent Barrier Coatings, 36th Annual Technical Conference Proceedings, 1993, ISBN 1-878068-12-1, pp. 302-305.

Kuhr, M. et al., Multifunktionsbeschichtungen fur innovative Applikationen von Kunststoff-Substraten, HiCotec Smart Coating Solutions, (2006).

Kulshreshtha, D.S., Specifications of a Spectroscopic Ellipsometer, Department of Physics & Astrophysics, University of Delhi, Delhi-110007, Jan. 16, 2009.

Krug, T.G., Transparent Barriers for Food Packaging, 33rd Annual Technical Conference Proceedings, 1990, ISBN 1-878068-09-1, pp. 163-169.

Lee, K. et al., The Ellipsometric Measurements of a Curved Surface, Japanese Journal of Applied Physics, vol. 44, No. 32, 2005, pp. L1015-L1018.

Lelait, L. et al., Microstructural Investigations of EBPVD Thermal Barrier Coatings, Journal De Physique IV, Colloque C9, supplément au Journal de Physique III, vol. 3, Dec. 1993, pp. 645-654.

Masso, J.D., Evaluation of Scratch Resistant and Antireflective Coatings for Plastic Lenses, 32nd Annual Technical Conference Proceedings, 1989, p. 237-240.

Misiano, C., et al., New Colourless Barrier Coatings (Oxygen & Water Vapor Transmission Rate) on Plastic Substrates, 35th Annual Technical Conference Proceedings, 1992, ISBN 1-878068-11-3, pp. 28-40.

Misiano, C., et al., Silicon Oxide Barrier Improvements on Plastic Substrate, Society of Vacuum Coaters, 34th Annual Technical Conference Proceedings, 1991, ISBN 1-878068-10-5, pp. 105-112.

Mount, E., Measuring Pinhole Resistance of Packaging, Corotec Corporation website, http://www.convertingmagazine.com, printed Jul. 13, 2009.

Murray, L. et al., The Impact of Foil Pinholes and Flex Cracks on the Moisture and Oxygen Barrier of Flexible Packaging, (2003).

Nelson, R.J., et al., Double-Sided QLF® Coatings for Gas Barriers, Society of Vacuum Coaters, 34th Annual Technical Conference Proceedings, 1991, ISBN 1-878068-10-5, pp. 113-117.

Nelson, R.J., Scale-Up of Plasma Deposited SiOx Gas Diffusion Barrier Coatings, 35th Annual Technical Conference Proceedings, 1992, ISBN 1-878068-11-3, pp. 75-78.

Novotny, V. J., Ultrafast Ellipsometric Mapping of Thin Films, IBM Technical Disclosure Bulletin, vol. 37, No. 02A, Feb. 1994, pp. 187-188.

Schultz, A. et al., Detection and Identification of Pinholes in Plasma-Polymerised Thin Film Barrier Coatings on Metal Foils, Surface & Coatings Technology 200, 2005, pp. 213-217.

Stchakovsky, M. et al., Characterization of Barrier Layers by Spectroscopic Ellipsometry for Packaging Applications, Horiba Jobin Yvon, Application Note, Spectroscopic Ellipsometry, SE 14, Nov. 2005.

Teboul, E., Thi-Film Metrology: Spectroscopic Ellipsometer Becomes Industrial Thin-Film Tool, LaserFocusWorld, http://www.laserfocusworld.com/display_article, printed Jul. 14, 2009.

Teyssedre, G. et al., Temperature Dependence of the Photoluminescence in Poly(Ethylene Terephthalate) Films, Polymer 42, 2001, pp. 8207-8216.

Tsung, L. et al., Development of Fast CCD Cameras for In-Situ Electron Microscopy, Microsc Microanal 14(Supp 2), 2008.

Wood, L. et al., A Comparison of SiO2 Barrier Coated Polypropylene to Other Coated Flexible Substrates, 35th Annual Technical Conference Proceedings, 1992, ISBN 1-878068-11-3, pp. 59-62.

Yang, et al., Microstructure and tribological properties of SiOx/DLC films grown by PECVD, Surface and Coatings Technology, vol. 194, Issue 1, Apr. 20, 2005, pp. 128-135.

AN 451, Accurate Thin Film Measurements by High-Resoluiton Transmission Electron Microscopy (HRTEM), Evans Alalytical Group, Version 1.0, Jun. 12, 2008, pp. 1-2.

Benefits of TriboGlide, TriboGlide Silicone-Free Lubrication Systems, http://www.triboglide.com/benfits.htm, printed Aug. 31, 2009.

Coating Syringes, http://www.triboglide.com/syringes.htm, printed Aug. 31, 2009.

Coating/Production Process, http:/lwww.triboglide.com/process.htm, printed Aug. 31, 2009.

Schott Developing Syringe Production in United States, Apr. 14, 2009, http://www.schott.com/pharmaceutical_packaging, printed Aug. 31, 2009.

Sterile Prefillable Glass and Polymer Syringes, Schott forma vitrum, http://www.schott.com/pharmaceutical_packaging, (2009).

European Patent Office, Communication with European Search Report, in Application No. 10162758.6, dated Aug. 19, 2010.

Griesser, Hans J., et al., Elimination of Stick-Slip of Elastomeric Sutures by Radiofrequency Glow Discharge Deposited Coatings, Biomed Mater. Res. Appl Biomater, 2000, vol. 53, 235-243, John Wiley & Sons, Inc.

European Patent Office, Communication with extended Search Report, in Application No. EP 10162761.0, dated Feb. 10, 2011.

European Patent Office, Communication with partial Search Report, in Application No. EP 10162758.6, dated Aug. 19, 2010.

European Patent Office, Communication with extended Search Report, in Application No. EP 10162758.6, dated Dec. 21, 2010.

Yang, et al., Microstructure and tribological properties of SiOx/DLC films grown by PECVD, Surface and Coatings Technology, vol. 194 (2005), Apr. 20, 2005, pp. 128-135.

European Patent Office, Communication with extended European search report, in Application No. EP10162756.0, dated Nov. 17, 2010.

Prasad, G.R. et al., "Biocompatible Coatings with Silicon and Titanium Oxides Deposited by PECVD", 3rd Mikkeli International Industrial Coating Seminar, Mikkeli, Finland, Mar. 16-18, 2006.

European Patent Office, Communication with extended European search report, in Application No. EP10162757.8, dated Nov. 10, 2010.

Patent Cooperation Treaty, Notification of Transmittal of the International Search Report and the Written Opinion of the International Searching Authority, in PCT/US2010/034568, dated Jan. 21, 2011.

Patent Cooperation Treaty, Notification of Transmittal of the International Search Report and the Written Opinion of the International Searching Authority, in PCT/US2010/034571, dated Jan. 26, 2011.

Patent Cooperation Treaty, Notification of Transmittal of the International Search Report and the Written Opinion of the International Searching Authority, in PCT/US2010/034576, dated Jan. 25, 2011.

Patent Cooperation Treaty, Notification of Transmittal of the International Search Report and the Written Opinion of the International Searching Authority, in PCT/US2010/034577, dated Jan. 21, 2011.

Patent Cooperation Treaty, Notification of Transmittal of the International Search Report and the Written Opinion of the International Searching Authority, in PCT/US2010/034582, dated Jan. 24, 2011.

European Patent Office, Communication with Extended Search Report, in Application No. EP 10162755.2, dated Nov. 9, 2010.

European Patent Office, Communication with Extended Search Report, in Application No. EP 10162760.2, dated Nov. 12, 2010.

PCT, Written Opinion of the International Searching Authority with International Search Report in Application No. PCT/US2010/034586, dated Mar. 15, 2011.

Shimojima, Atsushi et al., Structure and Properties of Multilayered Siloxane-Organic Hybrid Films Prepared Using Long-Chain Organotrialkoxysilanes Containing C=C Double Bonds, Journal of Materials Chemistry, 2007, vol. 17, pp. 658-663, © The Royal Society of Chemistry, 2007.

Sone, Hayato et al., Picogram Mass Sensor Using Resonance Frequency Shift of Cantilever, Japanese Journal of Applied Physics, vol. 43, No. 6A, 2004, pp. 3648-3651, © The Japan Society of Applied Physics.

(56) References Cited

OTHER PUBLICATIONS

Sone, Hayato et al., Femtogram Mass Sensor Using Self-Sensing Cantilever for Allergy Check, Japanese Journal of Applied Physics, vol. 45, No. 3B, 2006, pp. 2301-2304, © The Japan Society of Applied Physics.
Mallikarjunan, Anupama et al, The Effect of Interfacial Chemistry on Metal Ion Penetration into Polymeric Films, Mat. Res. Soc. Symp. Proc. vol. 734, 2003, © Materials Research Society.
Schonher, H., et al., Friction and Surface Dynamics of Polymers on the Nanoscale by AFM, STM and AFM Studies on (Bio)molecular Systems: Unravelling the Nanoworld. Topics in Current Chemistry, 2008, vol. 285, pp. 103-156, © Springer-Verlag Berlin Heidelberg.
Lang, H.P., Gerber, C., Microcantilever Sensors, STM and AFM Studies on (Bio)molecular Systems: Unravelling the Nanoworld. Topics in Current Chemistry, 2008, vol. 285, pp. 1-28, © Springer-Verlag Berlin Heidelberg.
Patent Cooperation Treaty, International Preliminary Examining Authority, Notification of Transmittal of International Preliminary Report on Patentability, in international application No. PCT/US2010/034571, dated Jun. 13, 2011.
Patent Cooperation Treaty, International Preliminary Examining Authority, Written Opinion of the International Preliminary Examining Authority, in international application No. PCT/US2010/034586, dated Aug. 23, 2011.
Patent Cooperation Treaty, International Preliminary Examining Authority, Written Opinion of the International Preliminary Examining Authority, in international application No. PCT/US2010/034568, dated May 30, 2011.
Patent Cooperation Treaty, Notification of Transmittal of International Preliminary Report on Patentability, in Application No. PCT/US2010/034576, dated Sep. 14, 2011.
Patent Cooperation Treaty, Notification of Transmittal of International Preliminary Report on Patentability, in Application No. PCT/US2010/034568, dated Sep. 14, 2011.
Patent Cooperation Treaty, International Search Report and Written Opinion, in Application No. PCT/US2011/036358, dated Sep. 9, 2011.
Patent Cooperation Treaty, International Search Report and Written Opinion, in Application No. PCT/US2011/036340, dated Aug. 1, 2011.
MacDonald, Gareth, "West and Daikyo Seiko Launch Ready Pack", http://www.in-pharmatechnologist.com/Packaging/West-and-Daikyo-Seiko-launch-Ready-Pack, 2 pages, retrieved from the internet Sep. 22, 2011.
Kumer, Vijai, "Development of Terminal Sterilization Cycle for Pre-Filled Cyclic Olefin Polymer (COP) Syringes", http://abstracts.aapspharmaceutica.com/ExpoAAPS09/CC/forms/attendee/index.aspx?content=sessionInfo&sessionId=401, 1 page, retrieved from the internet Sep. 22, 2011.
Quinn, F.J., "Biotech Lights Up the Glass Packaging Picture", http://www.pharmaceuticalcommerce.com/frontEnd/main.php?idSeccion=840, 4 pages, retrieved from the Internet Sep. 21, 2011.
Wen, Zai-Qing et al., Distribution of Silicone Oil in Prefilled Glass Syringes Probed with Optical and Spectroscopic Methods, PDA Journal of Pharmaceutical Science and Technology 2009, 63, pp. 149-158.
ZebraSci—Intelligent Inspection Products, webpage, http://zebrasci.com/index.html, retrieved from the internet Sep. 30, 2011.
Google search re "cyclic olefin polymer resin" syringe OR vial, http://www.google.com/search?sclient=psy-ab&hl=en&lr=&source=hp&q=%22cyclic+olefin+polymer+resin%22+syringe+OR+vial&btnG=Search&pbx=1&oq=%22cyclic+olefin+polymer+resin%22+syringe+OR+vial&aq, 1 page, retrieved from the internet Sep. 22, 2011.
Taylor, Nick, "West to Add CZ Vials as Glass QC Issues Drive Interest", ttp://twitter.com/WestPharma/status/98804071674281986, 2 pages, retrieved from the internet Sep. 22, 2011.
Silicone Oil Layer, Contract Testing, webpage, http://www.siliconization.com/downloads/siliconeoillayercontracttesting.pdf, retrieved from the internet Oct. 28, 2011.
Patent Cooperation Treaty, Notification of Transmittal of International Preliminary Report on Patentability, in PCT/US2010/034577, dated Nov. 24, 2011.
Patent Cooperation Treaty, Notification of Transmittal of International Preliminary Report on Patentability, in PCT/US2010/034582, dated Nov. 24, 2011.
Patent Cooperation Treaty, Notification of Transmittal of International Preliminary Report on Patentability, in PCT/US2010/034586, dated Dec. 20, 2011.
Patent Cooperation Treaty, Notification of Transmittal of the International Search Report and the Written Opinion of the International Searching Authority, in PCT/US2011/036097, dated Dec. 29, 2011.
"Oxford instruments plasmalab 80plus", XP55015205, retrieved from the Internet on Dec. 20, 2011, URL:http://www.oxfordplasma.de/pdf_inst/plas_80.pdf.
Patent Cooperation Treaty, Notification of Transmittal of the International Search Report and the Written Opinion of the International Searching Authority, in PCT/US2011/044215, dated Dec. 29, 2011.
European Patent Office, Communication pursuant to Article 94(3) EPC, in Application No. 10 162 758.6-1234, dated May 8, 2012 (6 pages).
Hanlon, Adriene Lepiane, Pak, Chung K., Pawlikowski, Beverly A., Decision on Appeal, Appeal No. 2005-1693, U.S. Appl. No. 10/192,333, dated Sep. 30, 2005.
Arganguren, Mirta I., Macosko, Christopher W., Thakkar, Bimal, and Tirrel, Matthew, "Interfacial Interactions in Silica Reinforced Silicones," Materials Research Society Symposium Proceedings, vol. 170, 1990, pp. 303-308.
Patent Cooperation Treaty, International Preliminary Examining Authority, Notification of Transmittal of International Preliminary Report on Patentability, in international application No. PCT/US2011/036097, dated Nov. 13, 2012.
Patent Cooperation Treaty, Written Opinion of the International Searching Authority with International Search Report in Application. No. PCT/US2012/064489, dated Jan. 25, 2013.
Danish Patent and Trademark Office, Singapore Written Opinion, in Application No. 201108308-6, dated Dec. 6, 2012.
Danish Patent and Trademark Office, Singapore Search Report, in Application No. 201108308-6, dated Dec. 12, 2012.
PCT, Written Opinion of the International Preliminary Examining Authority, in International application No. PCT/USUS13/048709, dated Sep. 30, 2014 (4 pages).
PCT, Notification of Transmittal of the International Preliminary Report on Patentability, in International application No. PCT/USUS13/048709, dated Oct. 15, 2014 (7 pages).
PCT, Written Opinion of the International Preliminary Examining Authority, in International application No. PCT/USUS13/064121, dated Nov. 19, 2014 (8 pages).
PCT, Written Opinion of the International Preliminary Examining Authority, in International application No. PCT/USUS13/064121, dated Nov. 21, 2014 (7 pages).
Intellectual Property Corporation of Malaysia, Substantive Examintion Adverse Report (section 30(1)/30(2)), in Application No. PI 2011005486, dated Oct. 31, 2014 (3 pages).
Patent Office of the Russian Federation, Official Action, in Application No. 2011150499, dated Sep. 25, 2014 (4 pages).
Instituto Mexicano de la Propiedad Indutrial, Official Action, in Appilcation No. MX/a/2012/013129, dated Sep. 22, 2014 (5 pages).
PCT, Notification of Transmittal of the International Search Report and the Written Opinion of the International Searching Authority, or the Declaration, in International application No. PCT/US2013/040380, dated Sep. 3, 2013. (13 pages).
PCT, Notification of Transmittal of the International Search Report and the Written Opinion of the International Searching Authority, or the Declaration, in International application No. PCT/US2013/040368, dated Oct. 21, 2013. (21 pages).
PCT, Notification of Transmittal of the International Search Report and the Written Opinion of the International Searching Authority, or the Declaration, in International application No. PCT/US2013/048709, dated Oct. 2, 2013. (7 pages).

(56) References Cited

OTHER PUBLICATIONS

Coclite A.M. et al., "On the relationship between the structure and the barrier performance of plasma deposited silicon dioxide-like films", Surface and Coatings Technology, Elsevier, Amsterdam, NL, vol. 204, No. 24, Sep. 15, 2010 (Sep. 15, 2010), pp. 4012-4017, XP027113381, ISSN: 0257-8972 [retrieved on Jun. 16, 2010] abstract, p. 4014, right-hand column—p. 4015, figures 2, 3.
Brunet-Bruneau A. et al., "Microstructural characterization of ion assisted Sio2 thin films by visible and infrared ellipsometry", Journal of Vacuum Science and Technology: Part A, AVS/AIP, Melville, NY, US, vol. 16, No. 4, Jul. 1, 1998 (Jul. 1, 1998), pp. 2281-2286, XP012004127, ISSN: 0734-2101, DOI: 10.1116/1. 581341, p. 2283, right-hand column—p. 2284, left-hand column, figures 2, 4.
Japanese Patent Office, Notice of Reason(s) for Rejection in Patent application No. 2012-510983, dated Jan. 7, 2014. (6 pages).
Chinese Patent Office, Notification of the Second Office Action in Application No. 201080029199.0, dated Jan. 6, 2014. (26 pages).
Chinese Patent Office, Notification of the First Office Action in Application No. 201180023474.2, dated Dec. 23, 2013. (18 pages).
PCT, Notification of Transmittal of the International Search Report and the Written Opinion of the International Searching Authority, or the Declaration, in International application No. PCT/US2013/067852, dated Jan. 22, 2014. (9 pages).
Sahagian, Khoren; Larner, Mikki; Kaplan, Stephen L., "Altering Biological Interfaces with Gas Plasma: Example Applications", Plasma Technology Systems, Belmont, CA, In SurFACTS in Biomaterials, Surfaces in Biomaterials Foundation, Summer 2013, 18(3), p. 1-5.
Daikyo Cyrystal Zenith Insert Needle Syringe System, West Delivering Innovative Services, West Pharmaceutical Services, Inc., 2010.
Daikyo Crystal Zenigh Syringes, West Pharmaceutical Services, Inc., www. WestPFSsolutions.com, #5659, 2011.
Zhang, Yongchao and Heller, Adam, Reduction of the Nonspecific Binding of a Target Antibody and of Its Enzyme-Labeled Detection Probe Enabling Electrochemical Immunoassay of Antibody through the 7 pg/mL—100 ng/mL (40 fM-400 pM) Range, Department of Chemical Engineering and Texas Materials Institute, University of Texas at Austin, Anal. Chem. 2005, 7, 7758-7762. (6 pages).
Principles and Applications of Liquid Scintillation Counting, LSC Concepts—Fundamentals of Liquid Scintillation Counting, National Diagnostics, 2004, pp. 1-15.
Chikkaveeraiah, Bhaskara V. and Rusling, Dr. James, Non Specific Binding (NSB) in Antigen-Antibody Assays, University of Connecticut, Spring 2007. (13 pages).
Sahagian, Khoren; Larner, Mikki; Kaplan, Stephen L., "Cold Gas Plasma in Surface Modification of Medical Plastics", Plasma Technology Systems, Belmont, CA, Publication pending. Presented at SPE Antec Medical Plastics Division, Apr. 23, 2013, Ohio.
Lipman, Melissa, "Jury Orders Becton to Pay $114M in Syringe Antitrust Case", © 2003-2013, Portfolio Media, Inc., Law360, New York (Sep. 20, 2013, 2:53 PM ET), http://www.law360.com/articles/474334/print?section=ip, [retrieved Sep. 23, 2013].
Wikipedia, the free encyclopedia, http://en.wikipedia.org/wiki/Birefringence, page last modified Sep. 18, 2013 at 11:39. [retrieved on Oct. 8, 2013]. (5 pages).
Wikipedia, the free encyclopedia, http://en.wikipedia.org/wiki/Confocal_microscopy, page last modified Aug. 28, 2013 at 11:12. [retrieved on Oct. 8, 2013]. (4 pages).
Wang, Jun et al., "Fluorocarbon thin film with superhydrophobic property prepared by pyrolysis of hexafluoropropylene oxide", Applied Surface Science, vol. 258, 2012, pp. 9782-9784 (4 pages)., (2005).
Wang, Hong et al., "Ozone-Initiated Secondary Emission Rates of Aldehydes from Indoor surfaces in Four Homes", American Chemical Society, Environmental Science & Technology, vol. 40, No. 17, 2006, pp. 5263-5268 (6 pages).

Lewis, Hilton G. Pryce, et al., "HWCVD of Polymers: Commercialization and Scale-Up", Thin Solid Films 517, 2009, pp. 3551-3554.
Wolgemuth, Lonny, "Challenges With Prefilled Syringes: The Parylene Solution", Frederick Furness Publishing, www.ongrugdelivery.com, 2012, pp. 44-45.
History of Panjlene (12 pages)., (2011).
SCS Parylene HTX brochure, Stratamet Thin Film Corporation, Fremont, CA, 2012, retrieved from the Internet Feb. 13, 2013, http://www.stratametthinfilm.com/parylenes/htx. (2 pages).
SCS Parylene Properties, Specialty Coating Systems, Inc., Indianapolis, IN, 2011. (12 pages).
Werthheimer, M.R., Studies of the earliest stages of plasma-enhanced chemical vapor deposition of SiO2 on polymeric substrates, Thin Solid Films 382 (2001) 1-3, and references therein, United States Pharmacopeia 34. In General Chapters <1>, 2001.
Gibbins, Bruce and Warner, Lenna, The Role of Antimicrobial Silver Nanotechnology, Medical Device & Diagnostic Industry, Aug. 205, pp. 2-6.
MTI CVD Tube Furnace w Gas Delivery & Vacuum Pump, http://mtixtl.com/MiniCVDTubeFurnace2ChannelsGasVacuum-OTF-1200X-S50-2F.aspx (2 pages)., (2005).
Lab-Built HFPO CVD Coater, HFPO Decomp to Give Thin Fluorocarbon Films, Applied Surface Science 2012 258 (24) 9782.
Technical Report No. 10, Journal of Parenteral Science and Technology, 42, Supplement 1988, Parenteral Formulation of Proteins and Peptides: Stability and Stabilizers, Parenteral Drug Association, 1988.
Technical Report No. 12, Journal of Parenteral Science and Technology, 42, Supplement 1988, Siliconization of Parenteral Drug Packaging Components, Parenteral Drug Association, 1988.
European Patent Office, Communication under Rule 71(3) EPC, in Application No. 10 162 760.2-1353, dated Oct. 25, 2013. (366 pages).
Wikipedia, the free encyclopedia, http://en.wikipedia.org/wiki/Difluorocarbene, page last modified Feb. 20, 2012 at 14:41. [retrieved on Sep. 7, 2012]. (4 pages).
O'Shaughnessy, W.S., et al., "Initiated Chemical Vapor Deposition of a Siloxane Coating for Insulation of Neutral Probes", Thin Solid Films 517 (2008) 3612-3614. (3 pages).
Denler, et al., Investigations of SiOx-polymer "interphases" by glancing angle RBS with Li+ and Be+ ions, Nuclear Instruments and Methods in Physical Research B 208 (2003) 176-180, United States Pharmacopeia 34. In General Chapters <1>, 2003.
PCT, Invitation to Pay Additional Fees and Annex to Form PCT/ISA/206 Communication relating to the results of the partial international search in International application No. PCT/US2013/071750, dated Feb. 14, 2014. (6 pages).
PCT, Notification of Transmittal of the International Search Report and the Written Opinion of the International Searching Authority, or the Declaration, in International application No. PCT/US2013/62247, dated Dec. 30, 2013. (13 pages).
PCT, Notification of Transmittal of the International Search Report and the Written Opinion of the International Searching Authority, or the Declaration, in International application No. PCT/US2013/043642, dated Dec. 5, 2013. (21 pages).
PCT, Notification of Transmittal of the International Search Report and the Written Opinion of the International Searching Authority, or the Declaration, in International application No. PCT/US2013/064121, dated Mar. 24, 2014. (8 pages).
PCT, Notification of Transmittal of the International Search Report and the Written Opinion of the International Searching Authority, or the Declaration, in International application No. PCT/US2013/070325, dated Mar. 24, 2014.
Japanese Patent Office, Notice of Reasons for Refusal, Patent Application No. 2013-510276, dated Mar. 8, 2016 (15 pages).
Australian Government, IP Australia, Patent Examination Report No. 1, in Application No. 2010249031, dated Mar. 13, 2014. (4 pages).
Australian Government, IP Australia, Patent Examination Report No. 1, in Application No. 2013202893, dated Mar. 13, 2014. (4 pages).

(56) References Cited

OTHER PUBLICATIONS

European Patent Office, Communication pursuant to Article 93(3) EPC, in Application No. 11 731 554.9 dated Apr. 15, 2014. (7 pages).
PCT, Notification Concerning Transmittal of International Preliminary Report on Patentability, in International application No. PCT/US2012/064489, dated May 22, 2014. (10 pages).
PCT, Notification of Transmittal of the International Search Report and the Written Opinion of the International Searching Authority, or the Declaration, in International application No. PCT/US2013/071750, dated Apr. 4, 2014. (13 pages).
PCT, Notification of Transmittal of the International Search Report and the Written Opinion of the International Searching Authority, or the Declaration, in International application No. PCT/US2014/019684, dated May 23, 2014. (16 pages).
PCT, Notification of Transmittal of the International Search Report and the Written Opinion of the International Searching Authority, or the Declaration, in International application No. PCT/US2014/023813, dated May 22, 2014. (11 pages).
European Patent Office, Communication pursuant to Article 94(3) EPC, in Application No. 11 736 511.4, dated Mar. 28, 2014.
PCT, Notification Concerning Transmittal of International Preliminary Report on Patentability, in International application No. PCT/US2011/042387, dated Jan. 17, 2013. (7 pages).
State Intellectual Property Office of the People's Republic of China, Notification of the First Office Action, in Application No. 201180032145.4, dated Jan. 30, 2014. (16 pages).
PCT, Notification Concerning Transmittal of International Preliminary Report on Patentability, in International application No. PCT/US2011/044215, dated Jan. 31, 2013. (14 pages).
Australian Government, Patent Examination Report No. 2 in Application No. 2010249031 dated Apr. 21, 2015.
Japanese Patent Office, Notice of Reasons for Refusal in application No. 2013-510276, dated Mar. 31, 2015.
Australian Government, IP Australia, Patent Examination Report No. 1, in Application No. 2012318242, dated Apr. 30, 2014. (6 pages).
State Intellectual Property Office of the People's Republic of China, Notification of the First Office Action, in Application No. 201180023461.5, dated May 21, 2014. (25 pages).
European Patent Office, Communication pursuant to Article 94(3) EPC, in Application No. 10162758.6 dated May 27, 2014. (7 pages).
PCT, Notification of Transmittal of the International Search Report and the Written Opinion of the International Searching Authority, or the Declaration, in International application No. PCT/US2014/029531, dated Jun. 20, 2014 (12 pages).
State Intellectual Property Office of the People's Republic of China, Notification of the Third Office Action, with translation, in Application No. 201080029199.0, dated Jun. 27, 2014 (19 pages).
Intellectual Property Office of Singapore, Invitation to Respond to Written Opinion, in Application No. 2012083077, dated Jun. 30, 2014 (12 pages).
PCT, Notification of Transmittal of International Preliminary Report on Patentability, in International application No. PCT/US13/40368, dated Jul. 16, 2014 (6 pages).
State Intellectual Property Office of the People's Republic of China, Notification of the Third Office Action, in Application No. 201080029201.4, dated Jul. 7, 2014 (15 pages).
Australian Government, IP Australia, Patent Examination Report No. 1, in Application No. 2011252925, dated Sep. 6, 2013 (3 pages).
Tao, Ran et al., Condensationand Polymerization of Supersaturated Monomer Vapor, ACS Publications, 2012 American Chemical Society, ex.doi.org/10.1021/la303462q/Langmuir 2012, 28, 16580-16587.
State Intellectual Property Office of TEH People's Republic of China, Notification of First Office Action in Application No. 201080029201.4, dated Mar. 37, 2013. (15 pages).
State Intellectual Property Office of the People's Republic of China, Notification of the Fourth Office Action in Application No. 201080029199.0, dated Mar. 18, 2015 (15 pages).
Hlobik, "Plastic Pre-Fillable Syringe Systems" (http://www.healthcarepackaging.com/package-type/Containers/plastic-prefillablesyringe-systems, Jun. 8, 2010).
PCT, Written Opinion of the International Preliminary Examining Authority, International application No. PCT/SU2013/071752, dated May 6, 2015.
Hopwood J Ed—CRC Press: "Plasma-assisted deposition", Aug. 17, 1997 (Aug. 17, 1997), Handbook of Nanophase Materials, Chapter 6, pp. 141-197, XP008107730, ISBN: 978-0-8247-9469-9.
Bose, Sagarika and Constable, Kevin, Advanced Delivery Devices, Design & Evaluation of a Polymer-Based Prefillable Syringe for Biopharmaceuticals With Improved Functionality & Performance, JR Automation Technologies, May 2015.
European Patent Office, Communication pursuant to Article 94(3) EPC, in Application No. 13 726 337.2, dated Dec. 2, 2016 (6 pages).

* cited by examiner

PECVD LUBRICITY VESSEL COATING, COATING PROCESS AND APPARATUS PROVIDING DIFFERENT POWER LEVELS IN TWO PHASES

CROSS-REFERENCE TO RELATED APPLICATIONS

This specification claims the priority of U.S. Ser. Nos. 61/792,952 and 61/800,494, each filed on Mar. 15, 2013. These entire applications are incorporated by reference here to provide continuity of disclosure.

FIELD OF THE INVENTION

The present invention relates to the technical field of fabrication of syringes and other medical devices having a lubricity coating applied by plasma enhanced chemical vapor deposition (PECVD), and more particularly to a method for applying a lubricity coating to an interior surface of a vessel using plasma enhanced chemical vapor deposition, to the use of a vessel processing system, to a computer-readable medium and to a program element.

BACKGROUND OF THE INVENTION

An important consideration when regarding syringes is to ensure that the plunger can move at a constant speed and with a constant force when it is pressed into the barrel. For this purpose, a lubricity layer, either on one or on both of the barrel and the plunger, is desirable. A similar consideration applies to vessels which have to be closed by a stopper, and to the stopper itself, and more generally to any surface which should provide a certain lubricity.

In glass syringes, silicon oil is typically used as a lubricant to allow the plunger to slide in the barrel. Silicon oil has been implicated in the precipitation of protein solutions such as insulin and some other biologics. Additionally, the silicon oil coating is often non-uniform, resulting in syringe failures in the market.

SUMMARY OF THE INVENTION

The present invention pertains to plastic vessels and medical devices, in particular vials and syringes, coated with thin PECVD coatings made from organosilicon precursors. These novel devices offer the superior barrier properties of glass and the dimensional tolerances and breakage resistance of plastics, yet reduce or eliminate the drawbacks of both materials. With designed modifications to the PECVD process, the surface chemistry of the coating can be predictably varied. In particular, a plasma coating ($SiO_xC_y$) is provided which improves lubricity ("lubricity coating"), thus eliminating the need for traditional silicon oil lubricants e.g. in syringes. Further embodiments of the invention are methods to influence the hydrophobicity/hydrophilicity of said coatings and the resulting coated devices.

An aspect of the invention is a method for preparing a lubricity coating on a plastic substrate, the method comprising: (a) providing a gas comprising an organosilicon precursor, and optionally an oxidant gas, and optionally a noble gas, in the vicinity of the substrate surface; and (b) generating a plasma in the gas by providing plasma-forming energy adjacent to the plastic substrate, thus forming a coating on the substrate surface by plasma enhanced chemical vapor deposition (PECVD).

The plasma-forming energy is applied in a first phase as a first pulse at a first energy level followed by further treatment in a second phase at a second energy level lower than the first energy level.

The invention further pertains to a substrate coated with the product of the above method, to a vessel processing system for coating of a vessel, the system comprising a processing station arrangement configured for performing the above and/or below mentioned method steps. Examples of such processing stations 5501-5504 are depicted in FIGS. 2-4.

The invention further pertains to a computer-readable medium, in which a computer program for coating of a vessel is stored which, when being executed by a processor of a vessel processing system, is adapted to instruct the processor to control the vessel processing system such that it carries out the above and/or below mentioned method steps.

The invention further pertains to a program element or computer program for coating of a vessel, which, when being executed by a processor of a vessel processing system, is adapted to instruct the processor to control the vessel processing system such that it carries out the above and/or below mentioned method steps.

The processor may thus be equipped to carry out exemplary embodiments of the methods of the present invention. The computer program may be written in any suitable programming language, for example, C++ and may be stored on the computer-readable medium, such as a CD-ROM. Also, the computer program may be available from a network, such as the Worldwide Web, from which it may be downloaded into image processing units or processors, or any suitable computers.

In the following, coating methods according to the invention and coated devices according to the invention which are made by these methods are described. The methods can be carried out on the equipment (vessel processing system and vessel holder) which is also described below.

Figures 1, 1A:
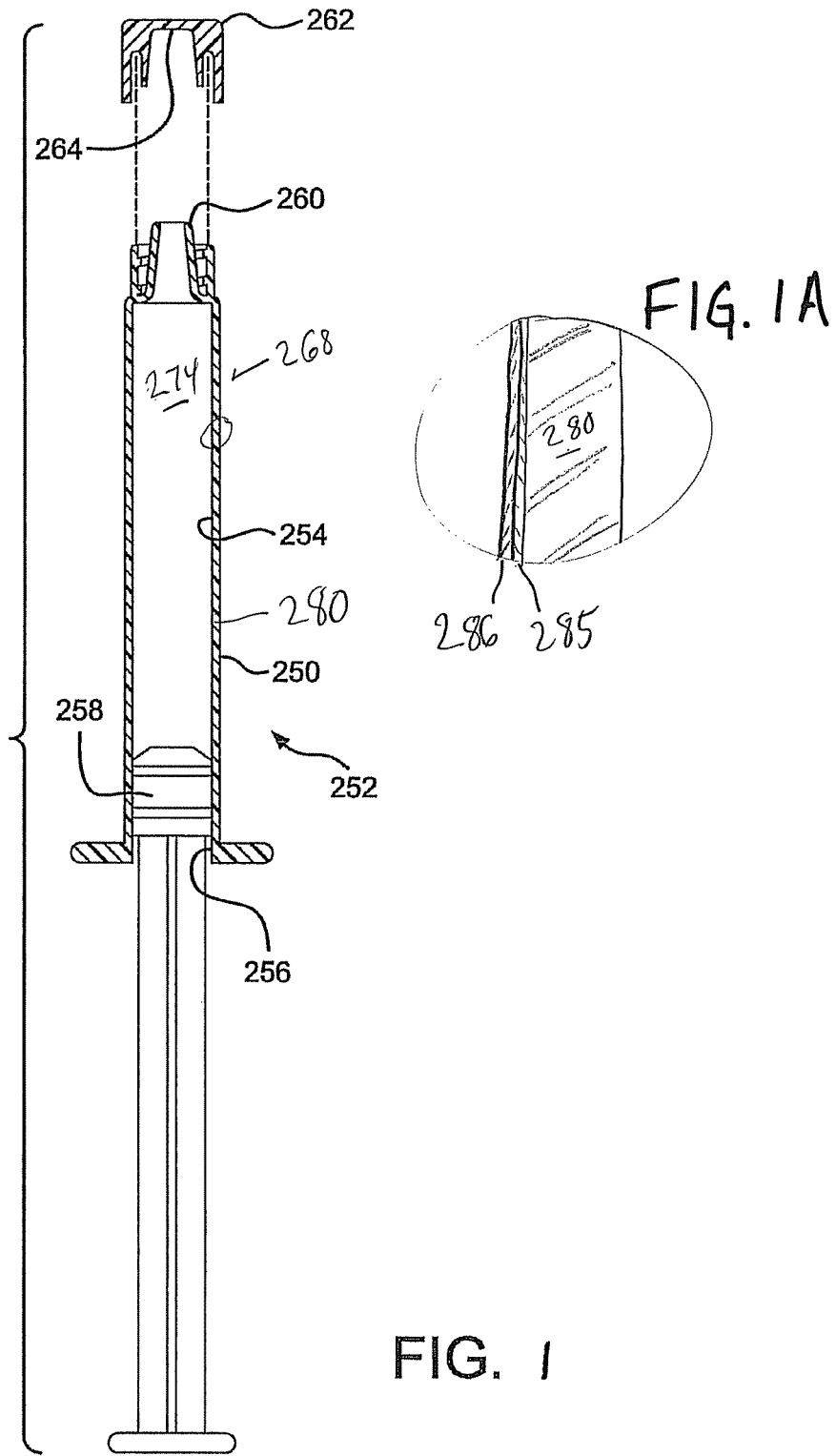
FIG. 1 is an exploded longitudinal sectional view of a syringe and cap adapted for use as a prefilled syringe.
FIG. 1A is an enlarged detail view of the syringe barrel wall of FIGS. 1, 7, and 8.

The following reference characters are used in the drawing figures:

| | |
|---|---|
| 20 | Vessel processing system |
| 38 | Vessel holder |
| 70 | Conveyor |

| | |
|---|---|
| 72 | Transfer mechanism (on) |
| 74 | Transfer mechanism (off) |
| 80 | Vessel |
| 108 | Probe (counter electrode) |
| 110 | Gas delivery port (of 108) |
| 250 | Syringe barrel |
| 252 | Syringe |
| 254 | Interior surface (of 250) |
| 256 | Back end (of 250) |
| 258 | Plunger (of 252) |
| 260 | Front end (of 250) |
| 262 | Cap |
| 264 | Interior surface (of 262) |
| 268 | Vessel |
| 270 | Closure |
| 272 | Interior facing surface |
| 274 | Lumen |
| 276 | Wall-contacting surface |
| 278 | Inner surface (of 280) |
| 280 | Vessel wall |
| 282 | Stopper |
| 284 | Shield |
| 285 | Underlying layer(s) |
| 286 | Lubricity layer |
| 288 | Barrier layer |
| 5501 | First processing station |
| 5502 | Second processing station |
| 5503 | Third processing station |
| 5504 | Fourth processing station |
| 5505 | Processor |
| 5506 | User interface |
| 5507 | Bus |
| 5701 | PECVD apparatus |
| 5702 | First detector |
| 5703 | Second detector |
| 5704 | Detector |
| 5705 | Detector |
| 5706 | Detector |
| 5707 | Detector |
| 7001 | Conveyor exit branch |
| 7002 | Conveyor exit branch |
| 7003 | Conveyor exit branch |
| 7004 | Conveyor exit branch |
| 7120 | Syringe |
| 7122 | Needle |
| 7124 | Barrel |
| 7126 | Cap |
| 7128 | Barrier coating |
| 7130 | Lubricity coating |
| 7132 | Outside surface |
| 7134 | Delivery outlet |
| 7136 | Base (of 22) |
| 7138 | Internal passage |
| 7140 | Generally cylindrical interior surface portion |
| 7142 | Generally hemispherical interior surface portion |
| 7144 | Front passage |
| 7146 | Lumen |
| 7148 | Lumen |
| 7150 | Ambient air |
| 7152 | Rim |
| 7154 | Exterior portion (of 7124) |
| 7156 | Opening |
| 7158 | Fluid |
| 7160 | Material (of 7124) |
| 7164 | Non-cylindrical portion (of 7122) |
| 7166 | Plunger |
| 7168 | Base |
| 7170 | Coupling |
| 7172 | Flexible lip seal |
| 7174 | Detent |
| 7176 | Projection |
| 7196 | Internal portion (of 7126) |
| 7198 | External portion (of 7126) |
| 71106 | Rear passage (of barrel) |
| 71110 | Tapered nose (of 7120) |
| 71112 | Tapered throat (of 7126) |
| 71114 | Collar (of syringe) |
| 71116 | Interior thread (of 71114) |
| 71118 | Dog (of 26) |
| 71120 | Dog (of 26) |
| 71122 | Syringe barrel |
| 71124 | Syringe cap |
| 71126 | (Syringe cap (flexible) |
| 71128 | Cap-syringe interface |
| 71130 | Syringe barrel |
| 71134 | Delivery outlet |
| 71136 | Base (of 22) |
| 71140 | Finger grip |
| 71144 | Flexible diaphragm |

DEFINITION SECTION

In the context of the present invention, the following definitions and abbreviations are used:

RF is radio frequency.

The term "at least" in the context of the present invention means "equal or more" than the integer following the term. The word "comprising" does not exclude other elements or steps, and the indefinite article "a" or "an" does not exclude a plurality unless indicated otherwise. Whenever a parameter range is indicated, it is intended to disclose the parameter values given as limits of the range and all values of the parameter falling within said range.

"First" and "second" or similar references to, e.g., processing stations or processing devices refer to the minimum number of processing stations or devices that are present, but do not necessarily represent the order or total number of processing stations and devices. These terms do not limit the number of processing stations or the particular processing carried out at the respective stations.

For purposes of the present invention, an "organosilicon precursor" is a compound having at least one of the linkage:

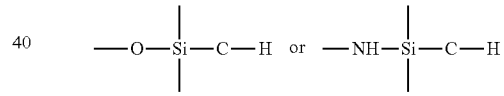

which is a tetravalent silicon atom connected to an oxygen or nitrogen atom and an organic carbon atom (an organic carbon atom being a carbon atom bonded to at least one hydrogen atom). A volatile organosilicon precursor, defined as such a precursor that can be supplied as a vapor in a PECVD apparatus, is an optional organosilicon precursor. Optionally, the organosilicon precursor is selected from the group consisting of a linear siloxane, a monocyclic siloxane, a polycyclic siloxane, a polysilsesquioxane, an alkyl trimethoxysilane, a linear silazane, a monocyclic silazane, a polycyclic silazane, a polysilsesquiazane, and a combination of any two or more of these precursors.

The feed amounts of PECVD precursors, gaseous reactant or process gases, and carrier gas are sometimes expressed in "standard volumes" in the specification and claims. The standard volume of a charge or other fixed amount of gas is the volume the fixed amount of the gas would occupy at a standard temperature and pressure (without regard to the actual temperature and pressure of delivery). Standard volumes can be measured using different units of volume, and still be within the scope of the present disclosure and claims. For example, the same fixed amount of gas could be expressed as the number of standard cubic centimeters, the number of standard cubic meters, or the number of standard cubic feet. Standard volumes can also be defined using different standard temperatures and pressures, and still be within the scope of the present disclosure and claims. For example, the standard temperature might be 0° C. and the standard pressure might be 760 Torr (as is conventional), or the standard temperature might be 20° C. and the standard pressure might be 1 Torr. But whatever standard is used in a given case, when comparing relative amounts of two or more different gases without specifying particular parameters, the same units of volume, standard temperature, and standard pressure are to be used relative to each gas, unless otherwise indicated.

The corresponding feed rates of PECVD precursors, gaseous reactant or process gases, and carrier gas are expressed in standard volumes per unit of time in the specification. For example, in the working examples the flow rates are expressed as standard cubic centimeters per minute, abbreviated as sccm. As with the other parameters, other units of time can be used, such as seconds or hours, but consistent parameters are to be used when comparing the flow rates of two or more gases, unless otherwise indicated.

A "vessel" in the context of the present invention can be any type of vessel with at least one opening and a wall defining an interior surface. The substrate can be the inside wall of a vessel having a lumen. Though the invention is not necessarily limited to vessels of a particular volume, vessels are contemplated in which the lumen has a void volume of from 0.5 to 50 mL, optionally from 1 to 10 mL, optionally from 0.5 to 5 mL, optionally from 1 to 3 mL. The substrate surface can be part or all of the inner surface of a vessel having at least one opening and an inner surface.

The term "at least" in the context of the present invention means "equal or more" than the integer following the term. Thus, a vessel in the context of the present invention has one or more openings. One or two openings, like the openings of a sample tube (one opening) or a syringe barrel (two openings) are preferred. If the vessel has two openings, they can be of same or different size. If there is more than one opening, one opening can be used for the gas inlet for a PECVD coating method according to the present invention, while the other openings are either capped or open. A vessel according to the present invention can be a syringe (or a part thereof, for example a syringe barrel) for storing or delivering a biologically active compound or composition, e.g. a medicament or pharmaceutical composition, a vial for storing biological materials or biologically active compounds or compositions, a pipe, e.g. a catheter for transporting biological materials or biologically active compounds or compositions, or a cuvette for holding fluids, e.g. for holding biological materials or biologically active compounds or compositions.

A vessel can be of any shape, a vessel having a substantially cylindrical wall adjacent to at least one of its open ends being preferred. Generally, the interior wall of the vessel is cylindrically shaped, like, e.g. in a sample tube or a syringe barrel. Sample tubes and syringes or their parts (for example syringe barrels) are contemplated.

A "hydrophobic layer" in the context of the present invention means that the coating lowers the wetting tension of a surface coated with the coating, compared to the corresponding uncoated surface. Hydrophobicity is thus a function of both the uncoated substrate and the coating. The same applies with appropriate alterations for other contexts wherein the term "hydrophobic" is used. The term "hydrophilic" means the opposite, i.e. that the wetting tension is increased compared to reference sample. The present hydrophobic layers are primarily defined by their hydrophobicity and the process conditions providing hydrophobicity, and optionally can have a composition according to the empirical composition or sum formula $Si_wO_xC_y$. It generally has an atomic ratio $Si_wO_xC_y$, wherein w is 1, x is from about 0.5 to about 2.4, y is from about 0.6 to about 3, preferably w is 1, x is from about 0.5 to 1.5, and y is from 0.9 to 2.0, more preferably w is 1, x is from 0.7 to 1.2 and y is from 0.9 to 2.0. The atomic ratio can be determined by XPS (X-ray photoelectron spectroscopy). Taking into account the H atoms, which are not measured by XPS, the coating may thus in one aspect have the formula $Si_wO_xC_yH_z$, for example where w is 1, x is from about 0.5 to about 2.4, y is from about 0.6 to about 3, and z is from about 2 to about 9.

These values of w, x, y, and z are applicable to the empirical composition $Si_wO_xC_yH_z$ throughout this specification. The values of w, x, y, and z used throughout this specification should be understood as ratios or an empirical formula (e.g. for a coating), rather than as a limit on the number or type of atoms in a molecule. For example, octamethylcyclotetrasiloxane, which has the molecular composition $Si_4O_4C_8H_{24}$, can be described by the following empirical formula, arrived at by dividing each of w, x, y, and z in the molecular formula by 4, the largest common factor: $Si_1O_1C_2H_6$. The values of w, x, y, and z are also not limited to integers. For example, (acyclic) octamethyltrisiloxane, molecular composition $Si_3O_2C_8H_{24}$, is reducible to $Si_1O_{0.67}C_{2.67}H_8$.

"Wetting tension" is a specific measure for the hydrophobicity or hydrophilicity of a surface. An optional wetting tension measurement method in the context of the present invention is ASTM D 2578 or a modification of the method described in ASTM D 2578. This method uses standard wetting tension solutions (called dyne solutions) to determine the solution that comes nearest to wetting a plastic film surface for exactly two seconds. This is the film's wetting tension. The procedure utilized is varied herein from ASTM D 2578 in that the substrates are not flat plastic films, but are tubes made according to the Protocol for Forming PET Tube and (except for controls) coated according to the Protocol for Coating Tube Interior with Hydrophobic Layer or coating (see Example 9 of EP2251671 A2).

A "lubricity layer" according to the present invention is a coating which has a lower frictional resistance than the uncoated surface. In other words, it reduces the frictional resistance of the coated surface in comparison to a reference surface that is uncoated. The present lubricity layers are primarily defined by their lower frictional resistance than the uncoated surface and the process conditions providing lower frictional resistance than the uncoated surface.

"Frictional resistance" can be static frictional resistance and/or kinetic frictional resistance.

One of the optional embodiments of the present invention is a syringe part, e.g. a syringe barrel or plunger, coated with a lubricity layer. In this contemplated embodiment, the relevant static frictional resistance in the context of the present invention is the breakout force as defined herein, and the relevant kinetic frictional resistance in the context of the present invention is the plunger sliding force as defined herein. For example, the plunger sliding force as defined and determined herein is suitable to determine the presence or absence and the lubricity characteristics of a lubricity layer or coating in the context of the present invention whenever the coating is applied to any syringe or syringe part, for example to the inner wall of a syringe barrel. The breakout force is of particular relevance for evaluation of the coating effect on a prefilled syringe, i.e. a syringe which is filled after coating and can be stored for some time, e.g. several months or even years, before the plunger is moved again (has to be "broken out").

The "plunger sliding force" (synonym to "glide force," "maintenance force," $F_m$, also used in this description) in the context of the present invention is the force required to maintain movement of a plunger in a syringe barrel, e.g. during aspiration or dispense. It can advantageously be determined using the ISO 7886-1:1993 test known in the art. A synonym for "plunger sliding force" often used in the art is "plunger force" or "pushing force".

The "plunger breakout force" (synonym to "breakout force", "break loose force", "initiation force", $F_i$, also used in this description) in the context of the present invention is the initial force required to move the plunger in a syringe, for example in a prefilled syringe.

Both "plunger sliding force" and "plunger breakout force" and methods for their measurement are described in more detail in subsequent parts of this description. These two forces can be expressed in N, lbs. or kg and all three units are used herein. These units correlate as follows: 1N=0.102 kg=0.2248 lbs. (pounds).

Sliding force and breakout force are sometimes used herein to describe the forces required to advance a stopper or other closure into a vessel, such as a medical sample tube or a vial, to seat the stopper in a vessel to close the vessel. Its use is analogous to use in the context of a syringe and its plunger, and the measurement of these forces for a vessel and its closure are contemplated to be analogous to the measurement of these forces for a syringe, except that at least in most cases no liquid is ejected from a vessel when advancing the closure to a seated position.

"Slidably" means that the plunger, closure, or other removable part is permitted to slide in a syringe barrel or other vessel.

DETAILED DESCRIPTION

The present invention will now be described more fully, inter alia with reference to the accompanying drawings, in which several embodiments are shown. This invention can, however, be embodied in many different forms and should not be construed as limited to the embodiments set forth here. Rather, these embodiments are examples of the invention, which has the full scope indicated by the language of the claims. Like numbers refer to like or corresponding elements throughout. The following disclosure relates to all embodiments unless specifically limited to a certain embodiment.

Referring to the drawings, a method for preparing a lubricity coating or layer 286 on a plastic substrate 280 such as the interior surface 254 of a vessel 268, 80, for example on its wall 280, is illustrated. When a vessel 268 is coated by the above coating method using PECVD, the coating method comprises several steps. A vessel 268 is provided having an open end, a closed end, and an interior surface. At least one gaseous reactant is introduced within the vessel 268. Plasma is formed within the vessel 268 under conditions effective to form a reaction product of the reactant, i.e. a coating, on the interior surface of the vessel 268.

Apparatus and general conditions suitable for carrying out this method are described in U.S. Pat. No. 7,985,188, which is incorporated here by reference in full.

The method includes providing a gas including an organosilicon precursor, optionally an oxidizing gas (for example $O_2$), and an inert gas in the vicinity of the substrate surface. The inert gas optionally is a noble gas, for example argon, helium, krypton, xenon, neon, or a combination of two or more of these inert gases. Plasma is generated in the gas by providing plasma-forming energy adjacent to the plastic substrate. As a result, a lubricity coating or layer 286 is formed on the substrate surface such as 254 by plasma enhanced chemical vapor deposition (PECVD). The plasmaforming energy is applied in a first phase as a first pulse at a first energy level, followed by further treatment in a second phase at a second energy level lower than the first energy level. Optionally, the second phase is applied as a second pulse.

Vessel

In any embodiment, the substrate optionally can be injection molded, blow molded, or otherwise formed from a polymer selected from the group consisting of a polycarbonate, an olefin polymer, a cyclic olefin copolymer (COC), a cyclic olefin polymer (COP), and a polyester, and preferably is a cyclic olefin polymer, a polyethylene terephthalate or a polypropylene, and more preferably is COP.

Another embodiment is a vessel 80, 268 including a barrier coating 288 and a closure 258, as well as a cap 262. The vessel 268 is generally tubular and made of thermoplastic material. The vessel 268 has a mouth or back end 256 and a lumen 274 bounded at least in part by a wall 280 having an inner surface interfacing with the lumen. There is an at least essentially continuous barrier coating 285 on the inner surface of the wall. A closure 258 covers the mouth and isolates the lumen of the vessel 268 from ambient air.

The vessel 268, 80 can also be made, for example of glass of any type used in medical or laboratory applications, such as soda-lime glass, borosilicate glass, or other glass formulations. Other vessels having any shape or size, made of any material, are also contemplated for use in the system 20. One function of coating a glass vessel can be to reduce the ingress of ions in the glass, either intentionally or as impurities, for example sodium, calcium, or others, from the glass to the contents of the vessel, such as a reagent or blood in an evacuated blood collection tube. Another function of coating a glass vessel in whole or in part, such as selectively at surfaces contacted in sliding relation to other parts, is to provide lubricity to the coating, for example to ease the insertion or removal of a stopper or passage of a sliding element such as a piston in a syringe. Still another reason to coat a glass vessel is to prevent a reagent or intended sample for the vessel, such as blood, from sticking to the wall of the vessel or an increase in the rate of coagulation of the blood in contact with the wall of the vessel.

A related embodiment is a vessel made of plastic, in which the barrier coating is made of soda lime glass, borosilicate glass, or another type of glass.

In any embodiment, the container size optionally can be from 1 to 10 mL, alternatively from 1 to 3 mL, alternatively from 6 to 10 mL.

One optional type of vessel 268 is a syringe including a plunger, a syringe barrel, and a lubricity coating as defined above on either one or both of these syringe parts, preferably on the inside wall of the syringe barrel. The syringe barrel includes a barrel having an interior surface slidably receiving the plunger. The lubricity coating may be disposed on the interior surface of the syringe barrel, or on the plunger surface contacting the barrel, or on both surfaces. The lubricity coating is effective to reduce the breakout force or the plunger sliding force necessary to move the plunger within the barrel.

The syringe optionally further includes a staked needle 7122. The needle is hollow with a typical size ranging from 18-29 gauge. The syringe barrel 250 has an interior surface slidably receiving the plunger. The staked needle may be affixed to the syringe during the injection molding of the syringe or may be assembled to the formed syringe using an adhesive. A cover 7126 is placed over the staked needle to seal the syringe assembly. The syringe assembly must be sealed so that a vacuum can be maintained within the syringe to enable the PECVD coating process.

As another option, the syringe can comprise a Luer fitting at its front end 260. The syringe barrel has an interior surface slidably receiving the plunger. The Luer fitting includes a Luer taper having an internal passage defined by an internal surface. The Luer fitting optionally can be formed as a separate piece from the syringe barrel and joined to the syringe barrel by a coupling.

Another aspect of the invention is a plunger for a syringe, including a piston 258, 7166 and a push rod. The piston has a front face, a generally cylindrical side face, and a back portion, the side face being configured to movably seat within a syringe barrel. The plunger has a lubricity coating according to the present invention on its side face. The push rod engages the back portion of the piston and is configured for advancing the piston in a syringe barrel. The plunger may additionally comprise an $SiO_x$ coating.

A further aspect of the invention is a vessel with just one opening, which can be, for example, a vessel for collecting or storing a compound or composition. Such vessel is in a specific aspect a tube, e.g. a sample collecting tube, e.g., a blood collecting tube. Such a tube may be closed with a closure, e.g. a cap or stopper. Such cap or stopper may comprise a lubricity coating according to the present invention on its surface which is in contact with the tube, and/or it may contain a passivating coating according to the present invention on its surface facing the lumen of the tube. In a specific aspect, such a stopper or a part thereof may be made from an elastomeric material.

A further particular aspect of the invention is a syringe barrel coated with the lubricity coating as defined in the preceding paragraph.

Gas Feed to PECVD Apparatus

A precursor is included in the gas feed provided to the PECVD apparatus. Preferably, the precursor is an organosilicon compound (in the following also designated as "organosilicon precursor"), more preferably an organosilicon compound selected from the group consisting of a linear siloxane, a monocyclic siloxane, a polycyclic siloxane, a polysilsesquioxane, an alkyl trimethoxysilane, an aza analogue of any of these precursors (i.e. a linear silazane, a monocyclic silazane, a polycyclic silazane, a polysilsesquioxazane), and a combination of any two or more of these precursors. The precursor is applied to a substrate under conditions effective to form a coating by PECVD. The precursor is thus polymerized, crosslinked, partially or fully oxidized, or any combination of these. In any embodiment, the organosilicon precursor optionally can include a linear or monocyclic siloxane, optionally comprising or consisting essentially of octamethylcyclotetrasiloxane (OMCTS), tetramethylcyclotetrasiloxane (TMCTS), hexamethyldisiloxane (HMDSO), tetramethyldisiloxane (TMDSO), or a combination of two or more of these.

The oxidizing gas can comprise or consist of oxygen ($O_2$ and/or $O_3$, the latter commonly known as ozone), nitrous oxide, or any other gas that oxidizes the precursor during PECVD at the conditions employed. The oxidizing gas comprises about 1 standard volume of oxygen. The gaseous reactant or process gas can be at least substantially free of nitrogen. In any embodiment. $O_2$ optionally can be present, preferably in a volume-volume ratio to the organosilicon precursor of from 0:1 to 2:1, optionally from 0:1 to 0.5:1, optionally from 0.01:1 to 0.5:1.

In any embodiment, Ar optionally can be present as the inert gas. The gas optionally can be from 1 to 6 standard volumes of the organosilicon precursor, from 1 to 100 standard volumes of the inert gas, and from 0.1 to 2 standard volumes of $O_2$. In any embodiment, both Ar and $O_2$ optionally can be present.

The method of the invention may comprise the application of one or more coatings made by PECVD from the same or different organosilicon precursors under the same or different reaction conditions. E.g. s syringe may first be coated with an $SiO_x$ barrier coating using HMDSO as organosilicon precursor, and subsequently with a lubricity coating using OMCTS as organosilicon precursor.

A gaseous reactant or process gas can be employed having a standard volume ratio of, for example when a lubricity coating is prepared:

from 1 to 6 standard volumes, optionally from 2 to 4 standard volumes, optionally equal to or less than 6 standard volumes, optionally equal to or less than 2.5 standard volumes, optionally equal to or less than 1.5 standard volumes, optionally equal to or less than 1.25 standard volumes of the precursor;

from 1 to 100 standard volumes, optionally from 5 to 100 standard volumes, optionally from 10 to 70 standard volumes, of a carrier gas;

from 0.1 to 2 standard volumes, optionally from 0.2 to 1.5 standard volumes, optionally from 0.2 to 1 standard volumes, optionally from 0.5 to 1.5 standard volumes, optionally from 0.8 to 1.2 standard volumes of an oxidizing agent.

First Phase of Plasma Forming Energy

In any embodiment, the plasma optionally can be generated with microwave energy or RF energy. The plasma optionally can be generated with electrodes powered at a radio frequency, preferably at a frequency of from 10 kHz to less than 300 MHz, more preferably of from 1 to 50 MHz, even more preferably of from 10 to 15 MHz, most preferably at 13.56 MHz.

In any embodiment, the first pulse energy can be, for example, from 21 to 100 Watts, alternatively from 25 to 75 Watts; alternatively from 40 to 60 Watts. The following first pulse energy ranges are alternatively contemplated: from 21 to 50 Watts; alternatively from 22 to 50 Watts; alternatively from 23 to 50 Watts; alternatively from 24 to 50 Watts; alternatively from 25 to 50 Watts; alternatively from 26 to 50 Watts; alternatively from 27 to 50 Watts; alternatively from 28 to 50 Watts; alternatively from 29 to 50 Watts; alternatively from 30 to 50 Watts; alternatively from 31 to 50 Watts; alternatively from 32 to 50 Watts; alternatively from 33 to 50 Watts; alternatively from 34 to 50 Watts; alternatively from 35 to 50 Watts; alternatively from 36 to 50 Watts; alternatively from 37 to 50 Watts; alternatively from 38 to 50 Watts; alternatively from 39 to 50 Watts; alternatively from 40 to 50 Watts; alternatively from 41 to 50 Watts; alternatively from 42 to 50 Watts; alternatively from 43 to 50 Watts; alternatively from 44 to 50 Watts; alternatively from 45 to 50 Watts; alternatively from 46 to 50 Watts; alternatively from 47 to 50 Watts; alternatively from 48 to 50 Watts; alternatively from 49 to 50 Watts; alternatively from 50 to 100 Watts; alternatively from 51 to 100 Watts; alternatively from 52 to 100 Watts; alternatively from 53 to 100 Watts; alternatively from 54 to 100 Watts; alternatively from 55 to 100 Watts; alternatively from 56 to 100 Watts; alternatively from 57 to 100 Watts; alternatively from 58 to 100 Watts; alternatively from 59 to 100 Watts; alternatively from 60 to 100 Watts; alternatively from 61 to 100 Watts; alternatively from 62 to 100 Watts; alternatively from 63 to 100 Watts; alternatively from 64 to 100 Watts; alternatively from 65 to 100 Watts; alternatively from 66 to 100 Watts; alternatively from 67 to 100 Watts; alternatively from 68 to 100 Watts; alternatively from 69 to 100 Watts; alternatively from 70 to 100 Watts; alternatively from 71 to 100 Watts; alternatively from 72 to 100 Watts; alternatively from 73 to 100 Watts; alternatively from 74 to 100 Watts; alternatively from 75 to 100 Watts; alternatively from 76 to 100 Watts; alternatively from 77 to 100 Watts; alternatively from 78 to 100 Watts; alternatively from 79 to 100 Watts; alternatively from 80 to 100 Watts; alternatively from 81 to 100 Watts; alternatively from 82 to 100 Watts; alternatively from 83 to 100 Watts; alternatively from 84 to 100 Watts; alternatively from 85 to 100 Watts; alternatively from 86 to 100 Watts; alternatively from 87 to 100 Watts; alternatively from 88 to 100 Watts; alternatively from 89 to 100 Watts; alternatively from 90 to 100 Watts; alternatively from 91 to 100 Watts; alternatively from 92 to 100 Watts; alternatively from 93 to 100 Watts; alternatively from 94 to 100 Watts; alternatively from 95 to 100 Watts; alternatively from 96 to 100 Watts; alternatively from 97 to 100 Watts; alternatively from 98 to 100 Watts; alternatively from 99 to 100 Watts; alternatively; alternatively from 21 to 99 Watts; alternatively from 21 to 98 Watts; alternatively from 21 to 97 Watts; alternatively from 21 to 96 Watts; alternatively from 21 to 95 Watts; alternatively from 21 to 94 Watts; alternatively from 21 to 93 Watts; alternatively from 21 to 92 Watts; alternatively from 21 to 91 Watts; alternatively from 21 to 90 Watts; alternatively from 21 to 89 Watts; alternatively from 22 to 88 Watts; alternatively from 23 to 87 Watts; alternatively from 24 to 86 Watts; alternatively from 25 to 85 Watts; alternatively from 21 to 84 Watts; alternatively from 21 to 83 Watts; alternatively from 21 to 82 Watts; alternatively from 21 to 81 Watts; alternatively from 21 to 80 Watts; alternatively from 21 to 79 Watts; alternatively from 22 to 78 Watts; alternatively from 23 to 77 Watts; alternatively from 24 to 76 Watts; alternatively from 26 to 74 Watts; alternatively from 27 to 73 Watts; alternatively from 28 to 72 Watts; alternatively from 29 to 71 Watts; alternatively from 30 to 70 Watts; alternatively from 31 to 69 Watts; alternatively from 32 to 68 Watts; alternatively from 33 to 67 Watts; alternatively from 34 to 66 Watts; alternatively from 35 to 65 Watts; alternatively from 36 to 64 Watts; alternatively from 37 to 63 Watts; alternatively from 38 to 62 Watts; alternatively from 39 to 61 Watts; alternatively from 41 to 59 Watts; alternatively from 42 to 58 Watts; alternatively from 43 to 57 Watts; alternatively from 44 to 56 Watts; alternatively from 45 to 55 Watts; alternatively from 46 to 54 Watts; alternatively from 47 to 53 Watts; alternatively from 48 to 52 Watts; alternatively from 49 to 51 Watts; alternatively 50 Watts.

In any embodiment, the ratio of the electrode power to the plasma volume for the first pulse optionally can be equal to or more than 5 W/ml, preferably is from 6 W/ml to 150 W/ml, more preferably is from 7 W/ml to 100 W/ml, most preferably from 7 W/ml to 20 W/ml.

In any embodiment, the first pulse optionally can be applied for 0.1 to 5 seconds, alternatively 0.5 to 3 seconds, alternatively 0.75 to 1.5 seconds. The first phase energy level optionally can be applied in at least two pulses. The second pulse is at a lower energy level than the first pulse. As a further option, the first phase energy level optionally can be applied in at least three pulses. The third pulse optionally can be at a lower energy level than the second pulse.

Second Phase of Plasma Forming Energy

In any embodiment, the second phase energy level optionally can be from 0.1 to 25 Watts, alternatively from 1 to 10 Watts, alternatively from 2 to 5 Watts.

Relation Between First and Second Phases

In any embodiment, the plasma-forming energy optionally can be applied in the first phase as a first pulse at a first energy level, followed by further treatment in a second phase at a second energy level.

Additional PECVD Treatment

In any embodiment, the contemplated method optionally includes a step for preparing a barrier coating an optional coating 285 on the substrate before the lubricity coating 286 is applied. The additional step optionally includes introducing a gas comprising an organosilicon precursor and $O_2$ in the vicinity of the substrate surface and generating plasma from the gas, thus forming an $SiO_x$ barrier coating on the substrate surface by plasma enhanced chemical vapor deposition (PECVD). Optionally, in the step for preparing a barrier coating, the plasma can be generated with electrodes powered with sufficient power to form an $SiO_x$ barrier coating on the substrate surface. The electrodes optionally are supplied with an electric power of from 8 to 500 W, preferably from 20 to 400 W, more preferably from 35 to 350 W, even more preferably of from 44 to 300 W, most preferably of from 44 to 70 W. In any embodiment of barrier coating, the $O_2$ optionally can be present in a volume: volume ratio of from 1:1 to 100:1 in relation to the silicon containing precursor, preferably in a ratio of from 5:1 to 30:1, more preferably in a ratio of from 10:1 to 20:1, even more preferably in a ratio of 15:1.

Another expedient contemplated here, for adjacent layers of $SiO_x$ and a lubricity layer or coating and/or hydrophobic layer, is a graded composite of $Si_wO_xC_y$, as defined in the Definition Section. A graded composite can be separate layers of a lubricity layer or coating and/or hydrophobic layer or coating and $SiO_x$ with a transition or interface of intermediate composition between them, or separate layers of a lubricity layer or coating and/or hydrophobic layer or coating and $SiO_x$ with an intermediate distinct layer or coating of intermediate composition between them, or a single layer or coating that changes continuously or in steps from a composition of a lubricity layer or coating and/or hydrophobic layer or coating to a composition more like $SiO_x$, going through the coating in a normal direction.

The grade in the graded composite can go in either direction. For example, a lubricity layer or coating and/or hydrophobic layer or coating can be applied directly to the substrate and graduate to a composition further from the surface of $SiO_x$. Or, the composition of $SiO_x$ can be applied directly to the substrate and graduate to a composition further from the surface of a lubricity layer or coating and/or hydrophobic layer. A graduated coating is particularly contemplated if a coating of one composition is better for adhering to the substrate than the other, in which case the better-adhering composition can, for example, be applied directly to the substrate. It is contemplated that the more distant portions of the graded coating can be less compatible with the substrate than the adjacent portions of the graded coating, since at any point the coating is changing gradually in properties, so adjacent portions at nearly the same depth of the coating have nearly identical composition, and more widely physically separated portions at substantially different depths can have more diverse properties. It is also contemplated that a coating portion that forms a better barrier against transfer of material to or from the substrate can be directly against the substrate, to prevent the more remote coating portion that forms a poorer barrier from being contaminated with the material intended to be barred or impeded by the barrier.

The coating, instead of being graded, optionally can have sharp transitions between one layer or coating and the next, without a substantial gradient of composition. Such coatings can be made, for example, by providing the gases to produce a layer or coating as a steady state flow in a non-plasma state, then energizing the system with a brief plasma discharge to form a coating on the substrate. If a subsequent coating is to be applied, the gases for the previous coating are cleared out and the gases for the next coating are applied in a steady-state fashion before energizing the plasma and again forming a distinct layer or coating on the surface of the substrate or its outermost previous coating, with little if any gradual transition at the interface.

Post-Treatment

Optionally, after the lubricity layer or coating is applied, it can be post-cured after the PECVD process. Radiation curing approaches, including UV-initiated (free radical or cationic), electron-beam (E-beam), and thermal as described in Development Of Novel Cycloaliphatic Siloxanes For Thermal And UV-Curable Applications (Ruby Chakraborty Dissertation, can 2008) be utilized. For example, in any embodiment, the lubricity coated container optionally can be further treated by post heating it, optionally at 50 to 110 degrees C., alternatively 80 to 100 degree C., optionally for a time interval of 1 to 72 hours, alternatively 4 to 48 hours, alternatively 8 to 32 hours, alternatively 20 to 30 hours. In any embodiment, the post heating step optionally can be carried out under at least partial vacuum, alternatively under a pressure of less than 50 Torr, alternatively under a pressure of less than 10 Torr, optionally under a pressure of less than 5 Torr, alternatively at a pressure of less than 1 Torr.

Properties

In any embodiment, the result of the present treatment can be a coated substrate coated with a lubricity coating. The lubricity coating optionally can have an average thickness of from 1 to 5000 nm, alternatively from 30 to 1000 nm, as another alternative from 100 to 500 nm. The optional $SiO_x$ barrier coating or layer of any embodiment optionally can have a thickness of from 20 to 30 nm.

These ranges are representing average thicknesses, as a certain roughness may enhance the lubricious properties of the lubricity coating. Thus its thickness is advantageously not uniform throughout the coating (see below). However, a uniformly thick lubricity coating is also considered.

The absolute thickness of the lubricity coating at single measurement points can be higher or lower than the range limits of the average thickness, with maximum deviations of preferably +/−50%, more preferably +/−25% and even more preferably +/−15% from the average thickness. However, it typically varies within the thickness ranges given for the average thickness in this description.

Figure 6:
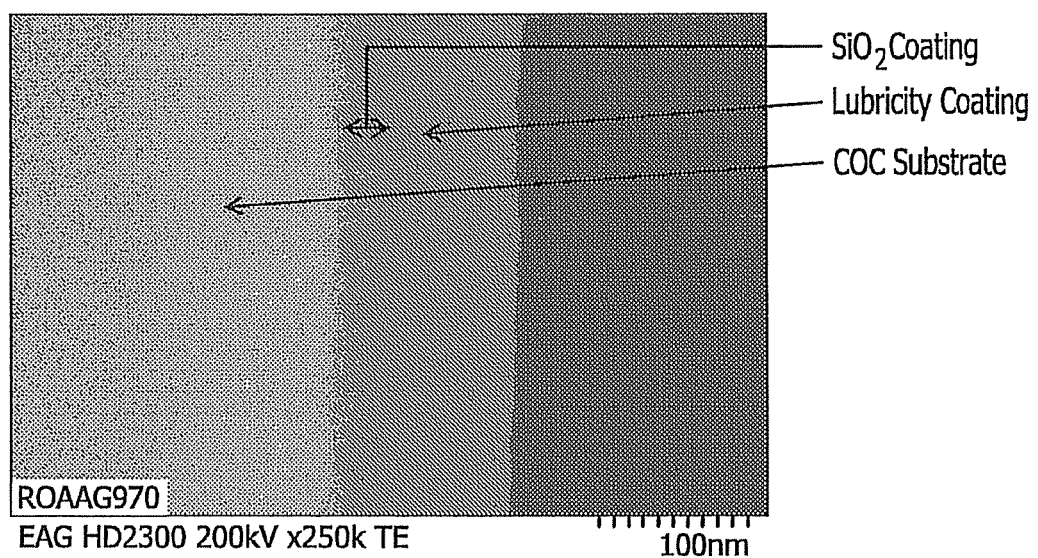
FIG. 6 shows a TEM image of a lubricity coating according to the invention coated on an $SiO_x$ barrier coating, which in turn is coated on a COC substrate.
Figure 7:
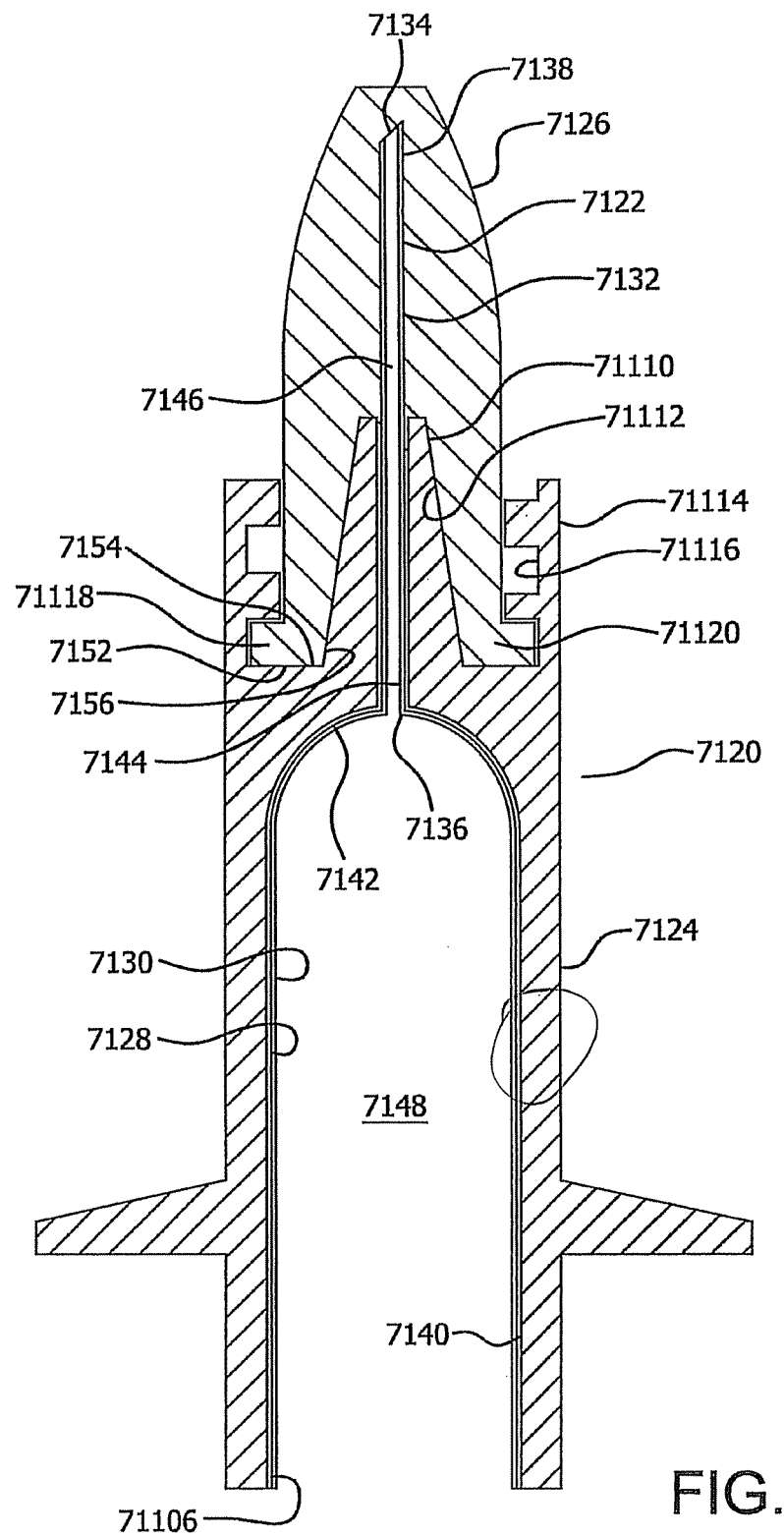
FIG. 7 is a longitudinal section of a syringe with a staked needle.
Figure 8:
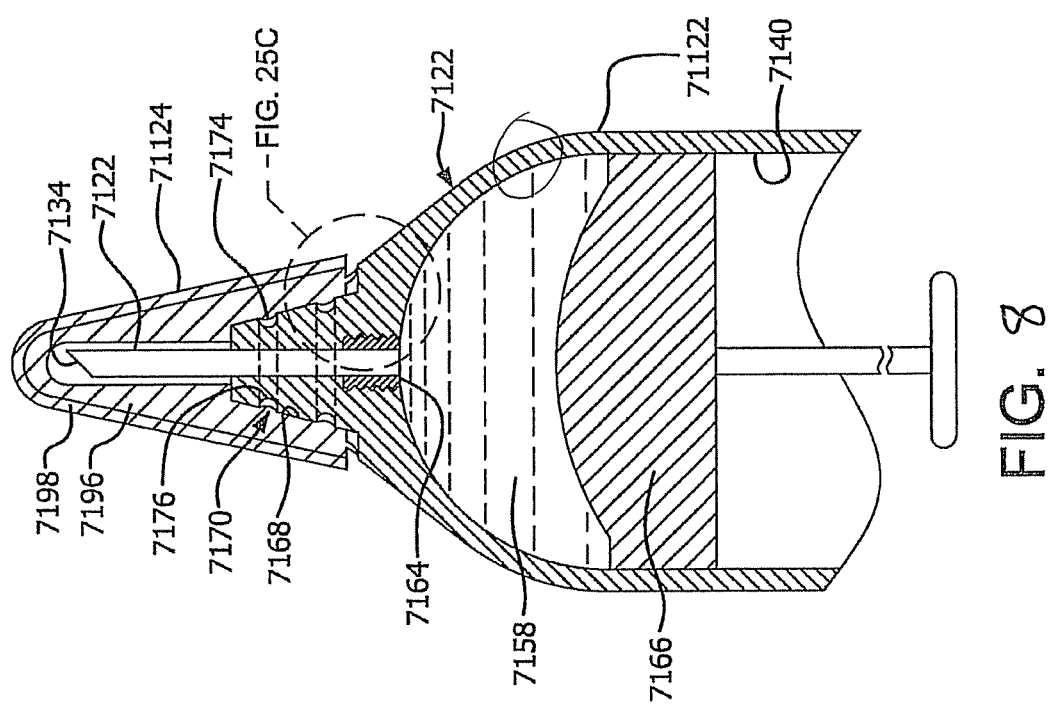
FIG. 8 is a fragmentary longitudinal section of the dispensing end of a prefilled syringe with a staked needle.

The thickness of this and other coatings can be measured, for example, by transmission electron microscopy (TEM). An exemplary TEM image for a lubricity coating is shown in FIG. 6.

The TEM can be carried out, for example, as follows. Samples can be prepared for Focused Ion Beam (FIB) cross-sectioning in two ways. Either the samples can be first coated with a thin layer or coating of carbon (50-100 nm thick) and then coated with a sputtered layer or coating of platinum (50-100 nm thick) using a K575X Emitech coating system, or the samples can be coated directly with the protective sputtered Pt layer. The coated samples can be placed in an FEI FIB200 FIB system. An additional layer or coating of platinum can be FIB-deposited by injection of an oregano-metallic gas while rastering the 30 kV gallium ion beam over the area of interest. The area of interest for each sample can be chosen to be a location half way down the length of the syringe barrel. Thin cross sections measuring approximately 15 μm ("micrometers") long, 2 μm wide and 15 μm deep can be extracted from the die surface using a proprietary in-situ FIB lift-out technique. The cross sections can be attached to a 200 mesh copper TEM grid using FIB-deposited platinum. One or two windows in each section, measuring ~8 μm wide, can be thinned to electron transparency using the gallium ion beam of the FEI FIB.

Cross-sectional image analysis of the prepared samples can be performed utilizing either a Transmission Electron Microscope (TEM), or a Scanning Transmission Electron Microscope (STEM), or both. All imaging data can be recorded digitally. For STEM imaging, the grid with the thinned foils can be transferred to a Hitachi HD2300 dedicated STEM. Scanning transmitted electron images can be acquired at appropriate magnifications in atomic number contrast mode (ZC) and transmitted electron mode (TE). The following instrument settings can be used.

| Instrument | Scanning Transmission Electron Microscope |
|---|---|
| Manufacturer/Model | Hitachi HD2300 |
| Accelerating Voltage | 200 kV |
| Objective Aperture | #2 |
| Condenser Lens 1 Setting | 1.672 |
| Condenser Lens 2 Setting | 1.747 |
| Approximate Objective Lens Setting | 5.86 |
| ZC Mode Projector Lens | 1.149 |
| TE Mode Projector Lens | 0.7 |
| Image Acquisition | |
| Pixel Resolution | 1280 × 960 |
| Acquisition Time | 20 sec.(×4) |

For TEM analysis the sample grids can be transferred to a Hitachi HF2000 transmission electron microscope. Transmitted electron images can be acquired at appropriate magnifications. The relevant instrument settings used during image acquisition can be those given below.

| Instrument | Transmission Electron Microscope |
|---|---|
| Manufacturer/Model | Hitachi HF2000 |
| Accelerating Voltage | 200 kV |
| Condenser Lens 1 | 0.78 |
| Condenser Lens 2 | 0 |
| Objective Lens | 6.34 |
| Condenser Lens Aperture | #1 |
| Objective Lens Aperture for imaging | #3 |
| Selective Area Aperture for SAD | N/A |

In any embodiment, optionally, the resulting lubricity coating optionally can have an atomic ratio $Si_wO_xC_y$ or $Si_wN_xC_y$ wherein w is 1, x is from about 0.5 to about 2.4, y is from about 0.6 to about 3.

The roughness of the lubricity coating is increased with decreasing power (in Watts) energizing the plasma, and by the presence of $O_2$ in the amounts described above. The roughness can be expressed as "RMS roughness" or "RMS" determined by AFM. RMS is the standard deviation of the difference between the highest and lowest points in an AFM image (the difference is designated as "Z"). It is calculated according to the formula:

$$Rq=\{\Sigma(Z_i-Z_{avg})2/N\}^{-2}$$

where $Z_{avg}$ is the average Z value within the image; $Z_1$ is the current value of Z; and N is the number of points in the image.

The RMS range in this specific embodiment is typically from 7 to 20 nm, preferably from 12 to 20 nm, optionally from 13 to 17 nm, optionally from 13 to 15 nm. A lower RMS can, however, still lead to satisfying lubricity properties. Alternatively, the resulting coating optionally can have a roughness when determined by AFM and expressed as RMS of from more than 0 to 25 nm, The coated substrate of any embodiment optionally can have a lower wetting tension than the uncoated surface, optionally a wetting tension of from 20 to 72 dyne/cm, optionally a wetting tension of from 30 to 60 dynes/cm, optionally a wetting tension of from 30 to 40 dynes/cm, optionally 34 dyne/cm. Optionally the coated substrate is more hydrophobic than the uncoated surface.

Optionally, the lubricity coating is a passivating coating, for example a hydrophobic coating resulting, e.g., in a lower precipitation of components of a composition in contact with the coated surface.

The plasma-forming energy optionally applied in the first phase optionally reduces the breakout force, $F_i$, of a syringe, compared to the breakout force of a similar syringe that has only been treated at the second energy level. The lubricity coating also has a lower frictional resistance $F_i$ than the uncoated surface. Optionally, the frictional resistance $F_i$ is reduced by at least 25%, or by at least 45%, or by at least 60% in comparison to the uncoated surface. Plunger sliding force can be measured, for example, as provided in the ISO 7886-1:1993 test. In order to achieve a sufficient lubricity (e.g. to ensure that a syringe plunger can be moved in the syringe, but to avoid uncontrolled movement of the plunger), the following ranges of $F_i$ and $F_m$ can advantageously be maintained:

$F_i$: 2.5 to 15 N;
$F_m$: 2.5 to 25 N.

The coated vessel 268 of any embodiment optionally can be a syringe comprising a barrel and a piston or plunger. The piston or plunger can have an outer surface engaging the inner surface of the barrel. At least one of the inner surface and outer surface can be a coated substrate according to any embodiment.

In a syringe of any embodiment, the plunger initiation force $F_i$ optionally can be from 2.5 to 15 N and the plunger maintenance force $F_m$ optionally can be from 2.5 to 25 N after 1 week.

In a syringe of any embodiment, the lubricity coating optionally can have the atomic ratio $Si_wO_xC_y$ or $Si_wN_xC_y$, wherein w is 1, x is from about 0.5 to about 2.4, y is from about 0.6 to about 3.

In a syringe of any embodiment, the lubricity coating optionally can have an average thickness of from 10 to 1000 nm.

The syringe or a syringe part in any embodiment optionally can be made according to any of the methods described in this specification. In an optional combination of features, the plastic substrate can be made of COC or COP, the gas can include octamethylcyclotetrasiloxane, $O_2$ and Ar, and the power for generating the plasma, in relation to the volume of the syringe lumen, can be from 6 W/ml to 0.1 W/ml.

The syringe in any embodiment optionally can contain a compound or composition in its lumen, preferably a biologically active compound or composition or a biological fluid, for example: (i) citrate or a citrate containing composition, (ii) a medicament, for example insulin or an insulin containing composition, or (iii) blood or blood cells.

For example, the present invention provides a method for setting the lubricity properties of a coating on a substrate surface, the method comprising the steps: (a) providing a gas comprising an organosilicon precursor and optionally $O_2$ and optionally an inert gas (e.g. Argon) in the vicinity of the substrate surface; and (b) generating a plasma from the gas by providing plasma-forming energy adjacent to the plastic substrate, thus forming a coating on the substrate surface by plasma enhanced chemical vapor deposition (PECVD). The lubricity characteristics of the coating are set by setting the ratio of the $O_2$ to the organosilicon precursor in the gaseous reactant, and/or by setting the electric power used for generating the plasma, and/or by setting the ratio of the noble gas to the organosilicon precursor.

Barrier Coating or Layer

In a further aspect of the invention, the coating further comprises a barrier coating, for example an $SiO_x$ coating. Typically, the barrier is against a gas or liquid, preferably against water vapor, oxygen and/or air. The barrier may also be used for establishing and/or maintaining a vacuum inside a vessel 268 coated with the barrier coating, e.g. inside a blood collection tube. In any embodiment, the coated substrate optionally can include at least one layer of $SiO_x$, wherein x is from 1.5 to 2.9, which optionally functions as a gas barrier coating.

The lubricity coating optionally can be situated between the $SiO_x$ layer and the substrate surface, or vice versa. The lubricity coating of present invention can optionally be applied onto an $SiO_x$ barrier coating. This is shown in FIG. 6, which contains a TEM picture of a lubricity coating on an $SiO_x$ layer.

Vessel Processing System

Figure 2:
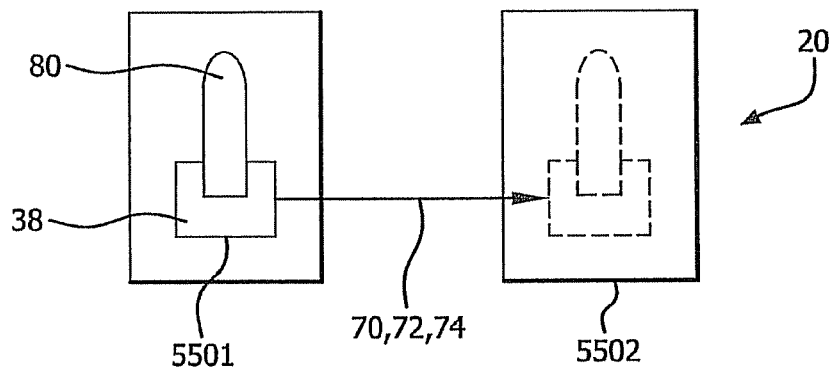
FIG. 2 shows a schematic representation of an exemplary vessel processing system.

In any embodiment a vessel processing system 20 is contemplated for coating a vessel 80. FIG. 2 shows a vessel processing system 20 according to an exemplary embodiment of the present invention. The system optionally can include a processing station arrangement (5501, 5502, 5503, 5504, 5505, 5506, 70, 72, 74) configured for performing any of the presently contemplated methods.

The first vessel processing station 5501 contains a vessel holder 38 which holds a seated vessel 268, 80. The vessel may also be a syringe body, a vial, a catheter or, for example, a pipette. The vessel may, for example, be made of glass or plastic. In case of plastic vessels, the first processing station may also comprise a mold for molding the plastic vessel.

After the first processing at the first processing station (which processing may comprise coating of the interior surface of the vessel, the vessel holder 38 may be transported together with the vessel 82 to the second vessel processing station 5502. This transportation is performed by a conveyor arrangement 70, 72, 74. For example, a gripper or several grippers may be provided for gripping the vessel holder 38 and/or the vessel 80 in order to move the vessel/holder combination to the next processing station 5502. Alternatively, only the vessel may be moved without the holder. However, it may be advantageous to move the holder together with the vessel in which case the holder is adapted such that it can be transported by the conveyor arrangement.

In any embodiment, a computer-readable medium is contemplated, in which a computer program for coating of a vessel 80 optionally can be stored. The program, when being executed by a processor of a vessel processing system 20, optionally can be adapted to instruct the processor to control the vessel processing system such that it carries out the contemplated method.

In any embodiment, a program element is contemplated for coating of a vessel 80. The program element optionally can be executed by a processor of a vessel processing system 20. The program element optionally can be adapted to instruct the processor to control the vessel processing system such that it carries out the contemplated method.

Figure 3:
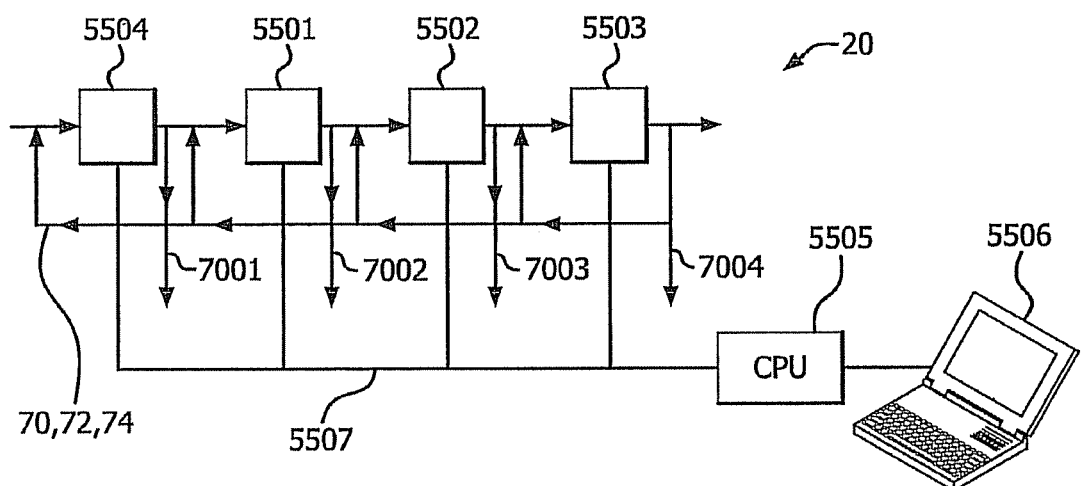
FIG. 3 shows a schematic representation of an exemplary vessel processing system.

FIG. 3 shows a vessel processing system 20 according to another exemplary embodiment of the present invention. Again, two vessel processing stations 5501, 5502 are provided. Furthermore, additional vessel processing stations 5503, 5504 may be provided which are arranged in series and in which the vessel can be processed, i.e. inspected and/or coated.

A vessel can be moved from a stock to the left processing station 5504. Alternatively, the vessel can be molded in the first processing station 5504. In any case, a first vessel processing is performed in the processing station 5504, such as a molding, an inspection and/or a coating, which may be followed by a second inspection. Then, the vessel is moved to the next processing station 5501 via the conveyor arrangement 70, 72, 74. Typically, the vessel is moved together with the vessel holder. A second processing is performed in the second processing station 5501 after which the vessel and holder are moved to the next processing station 5502 in which a third processing is performed. The vessel is then moved (again together with the holder) to the fourth processing station 5503 for a fourth processing, after which it is conveyed to a storage.

Before and after each coating step or molding step or any other step which manipulates the vessel an inspection of the whole vessel, of part of the vessel and in particular of an interior surface of the vessel may be performed. The result of each inspection can be transferred to a central processing unit 5505 via a data bus 5507. Each processing station is connected to the data bus 5507. The above described program element may run on the processor 5505, and the processor, which may be adapted in form of a central control and regulation unit, controls the system and may also be adapted to process the inspection data, to analyze the data and to determine whether the last processing step was successful.

If it is determined that the last processing step was not successful, because for example the coating comprises holes or because the surface of the coating is determined to be regular or not smooth enough, the vessel does not enter the next processing station but is either removed from the production process (see conveyor sections 7001, 7002, 7003, 7004) or conveyed back in order to become re-processed.

The processor 5505 may be connected to a user interface 5506 for inputting control or regulation parameters.

Figure 4:
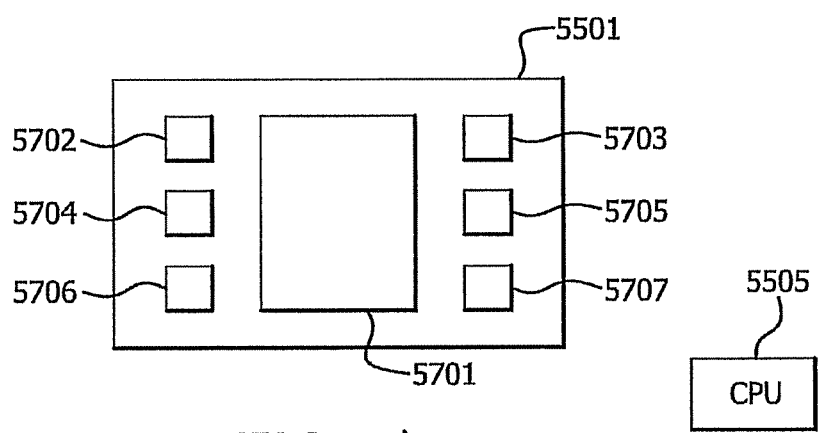
FIG. 4 shows a processing station of an exemplary vessel processing system.

FIG. 4 shows a vessel processing station 5501 according to an exemplary embodiment of the present invention. The station comprises a PECVD apparatus 5701 for coating an interior surface of the vessel. Furthermore, several detectors 5702-5707 may be provided for vessel inspection. Such detectors may for example be electrodes for performing electric measurements, optical detectors, like CCD cameras, gas detectors or pressure detectors.

Figure 5:
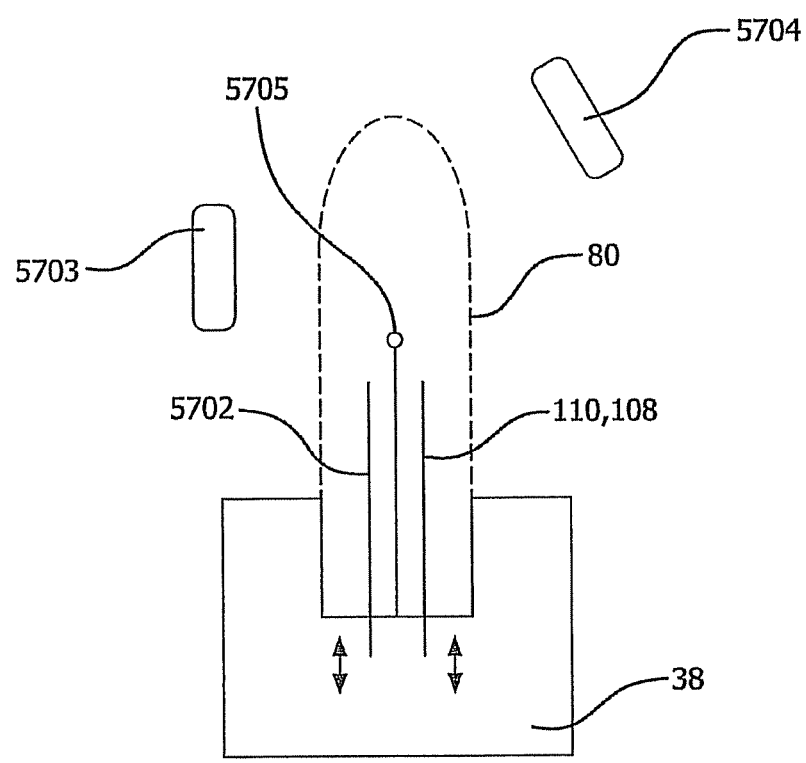
FIG. 5 shows a portable vessel holder.

FIG. 5 shows a vessel holder 38 according to an exemplary embodiment of the present invention, together with several detectors 5702, 5703, 5704 and an electrode with gas inlet port 108, 110.

The electrode and the detector 5702 may be adapted to be moved into the interior space of the vessel 80 when the vessel is seated on the holder 38.

The optical inspection may be particularly performed during a coating step, for example with the help of optical detectors 5703, 5704 which are arranged outside the seated vessel 80 or even with the help of an optical detector 5705 arranged inside the interior space of the vessel 80.

The detectors may comprise color filters such that different wavelengths can be detected during the coating process. The processing unit 5505 analyzes the optical data and determines whether the coating was successful or not to a predetermined level of certainty. If it is determined that the coating was most probably unsuccessful, the respective vessel is separated from the processing system or re-processed.

Product

The coated vessel of the invention may be empty, evacuated or (pre)filled with a compound or composition. One contemplated embodiment is a prefilled syringe, e.g. a syringe prefilled with a medicament, a diagnostic compound or composition, or any other biologically of chemically active compound or composition which is intended to be dispensed using the syringe.

The PECVD made coatings and PECVD coating methods using an organosilicon precursor described in this specification are also useful for coating catheters or cuvettes to form a barrier coating, a hydrophobic coating, a lubricity coating, or more than one of these. A cuvette is a small tube of circular or square cross section, sealed at one end, made of a polymer, glass, or fused quartz (for UV light) and designed to hold samples for spectroscopic experiments. The best cuvettes are as clear as possible, without impurities that might affect a spectroscopic reading. Like a test tube, a cuvette may be open to the atmosphere or have a cap to seal it shut. The PECVD-applied coatings of the present invention can be very thin, transparent, and optically flat, thus not interfering with optical testing of the cuvette or its contents.

Lubricity Profile

The lubricity coating optionally provides a consistent plunger force that reduces the difference between the break loose force ($F_i$) and the glide force ($F_m$). These two forces are important performance measures for the effectiveness of a lubricity coating. For $F_i$ and $F_m$, it is desired to have a low, but not too low value. With too low $F_i$, which means a too low level of resistance (the extreme being zero), premature/unintended flow may occur, which might e.g. lead to an unintentional premature or uncontrolled discharge of the content of a prefilled syringe.

Further advantageous $F_i$ and $F_m$ values can be found in the Tables of the Examples. Lower $F_i$ and $F_m$ values can be achieved than the ranges indicated above. Coatings having such lower values are also considered to be encompassed by the present invention.

Break-loose and glide forces are important throughout a device's shelf life especially in automated devices such as auto-injectors. Changes in break-loose and/or glide forces can lead to misfiring of auto injectors.

In a very particular aspect of the present invention, the lubricity is influenced by the roughness of the lubricity coating. It has surprisingly been found that a rough surface of the coating is correlated with enhanced lubricity. The roughness of the lubricity coating is increased with decreasing power (in Watts) energizing the plasma, and by the presence of $O_2$ in the amounts described above.

The vessels (e.g. syringe barrels and/or plungers) coated with a lubricity coating according to present invention have a higher lubricity, which means a lower $F_i$ and/or $F_m$ (determined, e.g. by measuring the $F_i$ and/or $F_m$) than the uncoated vessels. They also have a higher lubricity than vessels coated with an $SiO_x$ coating as described herein at the external surface.

Another aspect of the invention is a lubricity layer or coating deposited by PECVD from a feed gas comprising a monocyclic siloxane, a monocyclic silazane, a polycyclic siloxane, a polycyclic silazane, or any combination of two or more of these. The coating has an atomic concentration of carbon, normalized to 100% of carbon, oxygen, and silicon, as determined by X-ray photoelectron spectroscopy (XPS), greater than the atomic concentration of carbon in the atomic formula for the feed gas.

Optionally, the atomic concentration of carbon increases by from 1 to 80 atomic percent (as calculated and based on the XPS conditions in Example 15 of EP 2 251 455), alternatively from 10 to 70 atomic percent, alternatively from 20 to 60 atomic percent, alternatively from 30 to 50 atomic percent, alternatively from 35 to 45 atomic percent, alternatively from 37 to 41 atomic percent in relation to the atomic concentration of carbon in the organosilicon precursor when a lubricity coating is made.

An additional aspect of the invention is a lubricity layer or coating deposited by PECVD from a feed gas comprising a monocyclic siloxane, a monocyclic silazane, a polycyclic siloxane, a polycyclic silazane, or any combination of two or more of these. The coating has an atomic concentration of silicon, normalized to 100% of carbon, oxygen, and silicon, as determined by X-ray photoelectron spectroscopy (XPS), less than the atomic concentration of silicon in the atomic formula for the feed gas. See Example 15 of EP 2 251 455.

Optionally, the atomic concentration of silicon decreases by from 1 to 80 atomic percent (as calculated and based on the XPS conditions in Example 15 of EP 2251 455), alternatively from 10 to 70 atomic percent, alternatively from 20 to 60 atomic percent, alternatively from 30 to 55 atomic percent, alternatively from 40 to 50 atomic percent, alternatively from 42 to 46 atomic percent.

The lubricity coating can have a density between 1.25 and 1.65 g/cm$^3$, alternatively between 1.35 and 1.55 g/cm$^3$, alternatively between 1.4 and 1.5 g/cm$^3$, alternatively between 1.4 and 1.5 g/cm$^3$, alternatively between 1.44 and 1.48 g/cm$^3$, as determined by X-ray reflectivity (XRR).

SEM Procedure

Scanning electron microscope (SEM) Sample Preparation: Each syringe sample was cut in half along its length (to expose the interior surface). The top of the syringe (Luer end) was cut off to make the sample smaller.

The sample was mounted onto the sample holder with conductive graphite adhesive, then put into a Denton Desk IV SEM Sample Preparation System, and a thin (approximately 50 Å) thick gold coating was sputtered onto the interior surface of the syringe. The gold coating is required to eliminate charging of the surface during measurement.

The sample was removed from the sputter system and mounted onto the sample stage of a Jeol JSM 6390 SEM. The sample was pumped down to at least $1\times10^{-6}$ Torr in the sample compartment. Once the sample reached the required vacuum level, the slit valve was opened and the sample was moved into the analysis station.

The sample was imaged at a coarse resolution first, and then higher magnification images were accumulated. The SEM images provided in the Figures are 5 µm edge-to-edge (horizontal and vertical).

AFM (Atomic Force Microscopy) Procedure

AFM images were collected using a NanoScope III Dimension 3000 machine (Digital Instruments, Santa Barbara, Calif., USA). The instrument was calibrated against a NIST traceable standard. Etched silicon scanning probe microscopy (SPM) tips were used. Image processing procedures involving auto-flattening, plane fitting or convolution were employed. One 10 µm×10 µm area was imaged. Roughness analyses were performed and were expressed in: (1) Root-Mean-Square Roughness, RMS; (2) Mean Roughness, Ra; and (3) Maximum Height (Peak-to-Valley), Rmax, all measured in nm. For the roughness analyses, each sample was imaged over the 10 µm×10 µm area, followed by three cross sections selected by the analyst to cut through features in the 10 µm×10 µm images. The vertical depth of the features was measured using the cross section tool. For each cross section, a Root-Mean-Square Roughness (RMS) in nanometers was reported. These RMS values along with the average of the three cross sections for each sample are listed in Table 5.

Additional analysis of the 10 µm×10 µm images was carried out. For this analysis three cross sections were extracted from each image. The locations of the cross sections were selected by the analyst to cut through features in the images. The vertical depth of the features was measured using the cross section tool.

The Digital Instruments Nanoscope III AFM/STM acquires and stores 3-dimensional representations of surfaces in a digital format. These surfaces can be analyzed in a variety of ways.

The Nanoscope III software can perform a roughness analysis of any AFM or STM image. The product of this analysis is a single color page reproducing the selected image in top view. To the upper right of the image is the "Image Statistics" box, which lists the calculated characteristics of the whole image minus any areas excluded by a stopband (a box with an X through it). Similar additional statistics can be calculated for a selected portion of the image and these are listed in the "Box Statistics" in the lower right portion of the page. What follows is a description and explanation of these statistics.

Image Statistics

Z Range (Rp): The difference between the highest and lowest points in the image. The value is not corrected for tilt in the plane of the image; therefore, plane fitting or flattening the data will change the value.

Mean: The average of all of the Z values in the imaged area. This value is not corrected for the tilt in the plane of the image; therefore, plane fitting or flattening the data will change this value.

RMS (Rq): This is the standard deviation of the Z values (or RMS roughness) in the image. It is calculated according to the formula:

$$Rq = \{\Sigma(Z_i - Z_{avg})^2/N\}$$

where $Z_{avg}$ is the average Z value within the image; $Z_1$ is the current value of Z; and N is the number of points in the image. This value is not corrected for tilt in the plane of the image; therefore, plane fitting or flattening the data will change this value.

Mean roughness ($R_a$): This is the mean value of the surface relative to the Center Plane and is calculated using the formula:

$$R_a = [1/(L_x L_y)] \int o L_y \int o L_x \{f(x,y)\} dx dy$$

where f(x,y) is the surface relative to the Center plane, and $L_x$ and $L_y$ are the dimensions of the surface.

Max height ($R_{max}$): This is the difference in height between the highest and lowest points of the surface relative to the Mean Plane.

Surface area: (Optical calculation): This is the area of the 3-dimensional surface of the imaged area. It is calculated by taking the sum of the areas of the triangles formed by 3 adjacent data points throughout the image.

Surface area diff: (Optional calculation) This is the amount that the Surface area is in excess of the imaged area. It is expressed as a percentage and is calculated according to the formula:

$$\text{Surface area diff}=100[(\text{Surface area}/S_1^2)^{-1}]$$

where $S_1$ is the length (and width) of the scanned area minus any areas excluded by stopbands.

Center Plane: A flat plane that is parallel to the Mean Plane. The volumes enclosed by the image surface above and below the center plane are equal.

Mean Plane: The image data has a minimum variance about this flat plane. It results from a first order least squares fit on the Z data.

Protocol for Lubricity Testing

The following materials is used in this test:
Commercial (BD Hypak® PRTC) glass prefillable syringes with Luer-Lok® tip) (ca 1 mL)
COC syringe barrels made according to the Protocol for Forming COC Syringe barrel;
Commercial plastic syringe plungers with elastomeric tips taken from Becton Dickinson Product No. 306507 (obtained as saline prefilled syringes);
Normal saline solution (taken from the Becton-Dickinson Product No. 306507 prefilled syringes);
Dillon Test Stand with an Advanced Force Gauge (Model AFG-50N)
Syringe holder and drain jig (fabricated to fit the Dillon Test Stand)

The following procedure is used in this test.

The jig is installed on the Dillon Test Stand. The platform probe movement is adjusted to 6 in/min (2.5 mm/sec) and upper and lower stop locations were set. The stop locations were verified using an empty syringe and barrel. The commercial saline-filled syringes were labeled, the plungers were removed, and the saline solution is drained via the open ends of the syringe barrels for re-use. Extra plungers were obtained in the same manner for use with the COC and glass barrels.

Syringe plungers were inserted into the COC syringe barrels so that the second horizontal molding point of each plunger is even with the syringe barrel lip (about 10 mm from the tip end). Using another syringe and needle assembly, the test syringes were filled via the capillary end with 2-3 milliliters of saline solution, with the capillary end uppermost. The sides of the syringe were tapped to remove any large air bubbles at the plunger/fluid interface and along the walls, and any air bubbles were carefully pushed out of the syringe while maintaining the plunger in its vertical orientation.

The samples were created by coating COC syringe barrels according to the Protocol for Coating COC Syringe Barrel Interior with OMCTS Lubricity layer. An alternative embodiment of the technology herein, would apply the lubricity layer or coating over another thin film coating, such as $SiO_x$, for example applied according to the Protocol for Coating COC Syringe barrel Interior with $SiO_x$.

Instead of the Dillon Test Stand and drain jig, a Genesis Packaging Plunger Force Tester (Model SFT-01 Syringe Force Tester, manufactured by Genesis Machinery, Lionville, Pa.) can also be used following the manufacturer's instructions for measuring $F_i$ and $F_m$. The parameters that are used on the Genesis tester are:

Start: 10 mm
Speed: 100 mm/min
Range: 20
Units: Newtons

WORKING EXAMPLES

Example 1 and Comparative Example A

Embodiment Example 1 versus comparative Example A shows a benefit in lubricity, in particular the break loose force (Fi), obtained by initially applying the lubricity coating or layer using high power in first phase of a PECVD process, and then reducing the power in a second phase. For this test, 1 mL syringes were used with FluroTec plungers. Multiple syringes were coated with a lubricity coating under the conditions set out in the table entitled, "20 Watts vs. 50 Watts Power." The PECVD process was carried out in two phases, one following the other immediately, in the same equipment, without breaking vacuum between the two phases. In Phase 1, after allowing 15 seconds delay to allow the vacuum and gas flows to be established, PECVD was carried out at a power level of 20 Watts for one second in comparative Example A, and at a power level of 50 Watts for one second in Embodiment Example 1. In Phase 2, after a short additional delay both types of syringes were subjected to PECVD using the same gas mixture for similar times (the table noting a difference of 20 seconds of treatment for Example A vs. 15 seconds of treatment for Example 1).

Plungers were manually inserted in the syringes (although it has been found that manual insertion provides poorer results than automatic insertion, as discussed below). No plunger rods were used.

The treated syringes with plungers installed were then aged (put another way, the plungers were parked) for various periods of time up to a week, as indicated in the Table.

The lubricity performance ($F_i$, break loose force) of the respective samples was then tested, using a Genesis Packaging Plunger Force Tester (manufactured by Genesis Machinery, Lionville, Pa.). The equipment was used at a test speed of 300 mm/min.

As the Table, "20 Watts vs. 50 Watts Power," shows, the syringes of Example A initially treated at 20 Watts had a consistently higher $F_i$, thus requiring more force to break the plunger loose, than the syringes of Embodiment Example 1.

| Example | Delay (sec) | Power (W) | Time (sec) | OMCTS (sccm) | Oxygen (sccm) | Argon (sccm) |
|---|---|---|---|---|---|---|
| | | | Phase 1 | | | |
| A | 15 | 20 | 1 | 4 | 4 | 7.5 |
| 1 | 15 | 50 | 1 | 4 | 4 | 7.5 |
| | | | Phase 2 | | | |
| A | 3 | 2 | 20 | 4 | 4 | 7.5 |
| 1 | 3 | 2 | 15 | 4 | 4 | 7.5 |

| | Days Aged | | | | |
|---|---|---|---|---|---|
| Example | 0 | 0.1 | 1 | 3 | 7 |
| | Average $F_i$, N | | | | |
| A (20 W) | 7.63 | 11.59 | 15.3 | 16.49 | 18.17 |
| 1 (50 W) | 7.31 | 8.88 | 13.48 | 13.69 | 14.91 |

Examples 2 and 3 and Comparative Example B

Testing similar to that of Example 1 and Comparative Example A was carried out for Embodiment Examples 2 and 3 and Comparative Example B. This testing is summarized in the table entitled, Effect of Multi-Stage Process." In these tests, however, different power profiles were tested. For Comparative Example B, the Phase 1 power was 20 Watts applied for one second. For Embodiment Example 2, the Phase 1 power was 50 Watts. For Embodiment Example 3, the Phase 1 power was a first pulse at 50 Watts for one second, followed by a delay of 3 seconds, a second pulse at 30 Watts for 1 second, followed by a delay of 3 seconds, and a third pulse at 15 Watts for one second. For all three examples, the Phase 2 treatment was similar, except for the change in OMCTS flow rate for Example 2. This information is summarized in the Table.

The $F_i$ or break loose performance of the syringes was then tested essentially as described for Examples 1 and A, but with the following differences. The plungers used were Stelmi 6901 plungers. Standard plunger rods were used. The Genesis test speed was 100 mm/min.

The results are shown in the Table, "Effect of multi-stage process," which shows that a Phase 1 power level of 50 Watts in Example 2 provided lower $F_i$, thus better performance, at all comparable park times, than the Phase 1 power level of 20 Watts used in Example B. The three-level power stepdown of Phase 1 in Example 3 provided still better performance at all comparable park times.

| | | Effect of multi-stage process | | | | |
|---|---|---|---|---|---|---|
| Example | Delay (sec) | Power (W) | Time (sec) | OMCTS (sccm) | Oxygen (sccm) | Argon (sccm) |
| | | | Phase 1 | | | |
| B | 8 | 20 | 1 | 3.6 | 0.5 | 5 |
| 2 | 8 | 50 | 1 | 3 | 0.5 | 5 |
| 3 | 8 | 50/30/15 | 1/1/1 | 3 | 0.5 | 5 |
| | | | Phase 2 | | | |
| B | 3 | 5 | 10 | 3 | 0.5 | 5 |
| 2 | 3 | 5 | 10 | 3.6 | 0.5 | 5 |
| 3 | 3 | 5 | 10 | 3 | 0.5 | 5 |
| | | | Days Aging | | | |
| Example | 0 | 1 | 3 | 5 | 7 | |
| | | | Average $F_i$, N | | | |
| B | 11 | 25.9 | NA | 32.4 | 34.4 | |
| 2 | 5.4 | 13.9 | 17.9 | NA | 23.8 | |
| 3 | 4.1 | 11 | 13.5 | 19.9 | 21.9 | |

It is believed that this improvement occurs because the high-power first phase treatment conditions the thermoplastic substrate surface, allowing the subsequent second phase treatment at low power to Examples 4 and 5 and Comparative Examples C-E Testing similar to that of Example 1 and Comparative Example A was carried out for Embodiment Examples 4 and 5 and Comparative Examples C, D, and E. In these tests, however, after the syringes were coated and before they were tested for lubricity they were heated in an oven for 24 hours at 100° C. at a pressure of 1 Torr (gauge). This testing is summarized in the table entitled, "Oven Treatment."

| | | | | Oven Treatment | | | | |
|---|---|---|---|---|---|---|---|---|
| Example | OMCTS SCCM | Argon sccm | Oxygen sccm | Process Power Watts | Process Time (Sec) | Oven Treat | $F_i$ at 0 days N | $F_i$ at 7 days N |
| 4 | 4 | 10 | 6 | 3 | 10 | 100° C. 24 hours | 5.3 | 14.7 |
| 5 | 4 | 10 | 4 | 3 | 10 | 100° C. 24 hours | 4.6 | 14.5 |
| C | 4 | 10 | 4 | 3 | 10 | None | 3.2 | 18 |
| D | 4 | 10 | 6 | 3 | 10 | None | 3.1 | 18 |
| E | 4 | 10 | 2 | 3 | 10 | None | 3.2 | 18 |

As the Oven Treatment table shows, this treatment reduced and thus improved the break loose force, both initially (0 days) and after aging the lubricated syringes for 7 days.

Without limiting the invention according to the accuracy of this theory, it is believed that this improvement with oven treatment under vacuum occurs because the treatment drives more volatile constituents in the coating away, leaving a more durable baked on lubricity coating or layer. It is postulated that the improvement is due to driving off low molecular weight species from the lubricity layer, which would help limit the amount of molecular entanglements formed during aging. An increase in molecular entanglements over time is one potential mechanism associated with the break loose force aging phenomena.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for preparing a lubricity coating on a plastic substrate, the method comprising:
    (a) providing a gas comprising an organosilicon precursor, optionally an oxidizing gas, and an inert gas in the vicinity of the substrate surface;
    (b) generating plasma in the gas by applying plasma-forming energy adjacent to the plastic substrate as a first pulse at a first energy level; and
    (c) after said step (b), generating plasma in the gas by applying plasma-forming energy adjacent to the plastic substrate as a second pulse at a second energy level lower than the first energy level;

thus forming a coating on the substrate surface by plasma enhanced chemical vapor deposition (PECVD).

2. The method of claim 1, in which the first pulse energy level is from 21 to 100 Watts.

3. The method of claim 1, in which the first pulse is applied for 0.1 to 5 seconds.

4. The method of claim 1, in which the second pulse energy level is from 1 to 10 Watts.

5. The method of claim 1, in which the container size is from 1 to 10 mL.

6. The method of claim 1, in which the lubricity coated container is further treated by post heating it at 50 to 110 degrees C. for a time interval of 1 to 72 hours.

7. The method of claim 6, in which the post heating step is carried out under at least partial vacuum.

8. The method of claim 1, wherein the organosilicon precursor comprises a linear or monocyclic siloxane.

9. The method according to claim 1, wherein the oxidizing gas comprises $O_2$ present in a volume-volume ratio to the organosilicon precursor of from 0.01:1 to 0.5:1.

10. The method according to claim 1, wherein Ar is present as the inert gas.

11. The method according to claim 1, wherein the gas comprises from 1 to 6 standard volumes of the organosilicon precursor, from 1 to 100 standard volumes of the inert gas, and from 0.1 to 2 standard volumes of $O_2$.

12. The method according to claim 1, wherein both Ar and $O_2$ are present.

13. The method according to claim 1, wherein the resulting coating has a roughness when determined by AFM and expressed as RMS of from 7 to 20 nm.

14. The method according to claim 1, additionally comprising a step for preparing a barrier coating on the substrate before the lubricity coating is applied, the additional step comprising:
(a) providing a gas comprising an organosilicon precursor and an oxidizing gas in the vicinity of the substrate surface; and
(b) generating plasma from the gas, thus forming an $SiO_x$ barrier coating on the substrate surface by plasma enhanced chemical vapor deposition (PECVD).

15. The method according to claim 14 wherein in the step for preparing a barrier coating
(i) the plasma is generated with electrodes powered with sufficient power to form an $SiO_x$ barrier coating on the substrate surface; and
(ii) the ratio of the electrode power to the plasma volume is equal or more than 5 W/ml; and/or
(iii) the oxidizing gas comprises $O_2$ in a volume:volume ratio of from 1:1 to 100:1 in relation to the silicon containing precursor.

16. The method according to claim 1, wherein the substrate is a polymer selected from the group consisting of a polycarbonate, an olefin polymer, a cyclic olefin copolymer (COC), a cyclic olefin polymer (COP), and a polyester.

17. The method according to claim 1, wherein the plasma is generated with RF energy.

18. The method according to claim 1, wherein the plasma-forming energy reduces the breakout force, $F_i$, of the syringe, compared to the breakout force of a similar syringe that has only been treated at the second energy level.

19. The method according to claim 1, wherein the resulting lubricity coating has an atomic ratio $Si_wO_xC_y$ or $Si_wN_xC_y$ wherein w is 1, x is from about 0.5 to about 2.4, y is from about 0.6 to about 3.

20. A coated substrate coated with a lubricity coating made by the method according to claim 1.

21. The coated substrate of claim 20, wherein the lubricity coating has a lower frictional resistance than the uncoated surface by at least 25%.

22. A syringe comprising a barrel made according to claim 1.

23. The syringe according to claim 22 which contains in its lumen a medicament.

24. The syringe of claim 22, wherein the plunger initiation force $F_i$ is from 2.5 to 15 N and the plunger maintenance force $F_m$ is from 2.5 to 25 N after 1 week.

25. The method of claim 1 wherein the lubricity coating has the atomic ratio $Si_wO_xC_y$ wherein w is 1, x is from about 0.5 to about 2.4, y is from about 0.6 to about 3.

26. The method of claim 1, wherein the plastic substrate is COP, wherein the gas in step (a) comprises octamethylcyclotetrasiloxane, $O_2$ and Ar, and wherein the power for generating the plasma is from 6 W/ml to 0.1 W/ml in relation to the volume of the syringe lumen.

27. A method for preparing a lubricity coating on a plastic substrate, the method comprising:
(a) providing plasma enhanced chemical vapor deposition (PECVD) equipment;
(b) in the plasma enhanced chemical vapor deposition (PECVD) equipment, providing a gas comprising an organosilicon precursor, optionally an oxidizing gas, and an inert gas in the vicinity of the substrate surface;
(c) in the plasma enhanced chemical vapor deposition (PECVD) equipment, generating plasma in the gas by providing plasma-forming energy adjacent to the plastic substrate as a first pulse at a first energy level; and
(d) after step (c), in the same plasma enhanced chemical vapor deposition (PECVD) equipment, without breaking vacuum, generating plasma in the gas by providing plasma-forming energy adjacent to the plastic substrate as a second pulse at a second energy level lower than the first energy level;

thus forming a coating on the substrate surface by plasma enhanced chemical vapor deposition (PECVD).

28. The method of claim 1, in which the first pulse is applied for 0.1 to 5 seconds and the first pulse energy level is from 21 to 100 Watts.

* * * * *